United States Patent [19]

Roch et al.

[11] Patent Number: 4,518,596
[45] Date of Patent: May 21, 1985

[54] ANTITHROMBOTIC USE OF 2-(PERHYDRO-1,4-DIAZINO)-PYRIMIDO (5,4,D)-PYRIMIDINES

[75] Inventors: Josef Roch; Erich Müller; Berthold Narr; Josef Nickl; Walter Haarmann; Johannes M. Weisenberger, all of Biberach, Fed. Rep. of Germany

[73] Assignee: Dr. Karl Thomae GmbH, Biberach an der Riss, Fed. Rep. of Germany

[21] Appl. No.: 575,333

[22] Filed: Jan. 31, 1984

Related U.S. Application Data

[63] Continuation-in-part of Ser. No. 350,429, Feb. 22, 1982, abandoned, which is a continuation of Ser. No. 161,010, Jun. 19, 1980, abandoned.

[30] Foreign Application Priority Data

Jul. 3, 1979 [DE] Fed. Rep. of Germany ....... 2926804
Apr. 11, 1980 [DE] Fed. Rep. of Germany ....... 3013930

[51] Int. Cl.³ ............... A61K 31/535; A61K 31/54
[52] U.S. Cl. .................... 514/232; 544/58.2; 544/58.6; 544/61; 514/222; 514/230; 514/822
[58] Field of Search ............ 544/58.2, 58.6, 61, 544/118; 424/246, 248.52, 248.51, 248.54, 248.56, 248.57, 248.58

[56] References Cited

U.S. PATENT DOCUMENTS 3,031,450 4/1962 Fischer et al. ................ 544/118

FOREIGN PATENT DOCUMENTS 209344 5/1960 Austria .

OTHER PUBLICATIONS

Goodman et al., *The Pharmacological Basis of Therapeutics*, Fifth Edition, pp. XIII, XV, 653, 1308.

*Primary Examiner*—Robert W. Ramsuer
*Attorney, Agent, or Firm*—Hammond & Littell, Weissenberger & Dippert

[57] ABSTRACT

Compounds of the formula

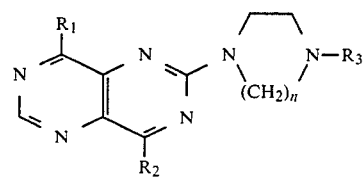

wherein
$R_1$ is a substituted alkoxy group, or an optionally substituted mercapto or amino group,
$R_2$ is a cyclic imino group,
$R_3$ is hydrogen, phenyl, alkyl or acyl, and
n is 2 or 3, and non-toxic, pharmacologically acceptable acid addition salts thereof; the compounds as well as their salts are useful as antithrombotics.

5 Claims, No Drawings

ANTITHROMBOTIC USE OF 2-(PERHYDRO-1,4-DIAZINO)-PYRIMIDO (5,4,D)-PYRIMIDINES

This is a continuation-in-part of co-pending application Ser. No. 350,429, filed Feb. 22, 1982, now abandoned; which in turn is a continuation of application Ser. No. 161,010, filed June 19, 1980, now abandoned.

This invention relates to novel 2-(perhydro-1,4-diazino)-pyrimido[5,4-d]pyrimidines and non-toxic acid addition salts thereof, to methods of preparing these compounds, to pharmaceutical compositions containing them as active ingredients, and to methods of using them as antithrombotics.

More particularly, the present invention relates to a novel class of compounds represented by the formula

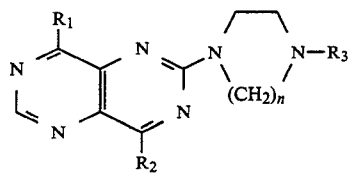

wherein
$R_1$ is —O—$R_4$, —S—$R_5$ or

$R_2$ is thiomorpholino, methyl-thiomorpholino, dimethyl-thiomorpholino, thiomorpholino-1-oxide, methyl-thiomorpholino-1-oxide, dimethyl-thiomorpholino-1-oxide, thiomorpholino-1,1-dioxide, methyl-thiomorpholino-1,1-dioxide or dimethyl-thiomorpholino-1,1-dioxide;

one of $R_1$ and $R_2$ is morpholino, methyl-morpholino or dimethyl-morpholino and the other of $R_1$ and $R_2$ has the meaning previously defined.

$R_3$ is hydrogen, phenyl, alkyl of 1 to 5 carbon atoms, hydroxy-(alkyl of 1 to 5 carbon atoms), phenyl-(alkyl of 1 to 5 carbon atoms), alkanoyl of 2 to 4 carbon atoms), methoxy-(alkanoyl of 2 to 4 carbon atoms), acetyl-(alkanoyl of 2 to 4 carbon atoms), carboxy-(alkanoyl of 2 to 4 carbon atoms), formyl, acetoxybenzoyl, pyridinoyl, furoyl or thenoyl;

n is 2 or 3;

$R_4$ is alkyl of 1 to 3 carbon atoms, hydroxy-(alkyl of 1 to 3 carbon atoms), (alkoxy of 1 to 3 carbon atoms)-carbonyl-(alkyl of 1 to 3 carbon atoms), phenyl-(alkyl of 1 to 3 carbon atoms), (alkyl of 1 to 3 carbon atoms)-mercaptophenyl-(alkyl of 1 to 3 carbon atoms) or di(alkyl of 1 to 3 carbon atoms) amino-(alkyl of 1 to 3 carbon atoms;

$R_5$ is alkyl of 1 to 8 carbon atoms; hydroxy-(alkyl of 1 to 3 carbon atoms); (alkoxy of 1 to 3 carbon atoms)-carbonyl-(alkyl of 1 to 3 carbon atoms); phenyl-(alkyl of 1 to 3 carbon atoms); (alkyl of 1 to 3 carbon atoms)-mercaptophenyl-(alkyl of 1 to 3 carbon atoms); di(alkyl of 1 to 3 carbon atoms) amino-(alkyl of 1 to 3 carbon atoms; hydrogen; cycloalkyl of 5 to 7 carbon atoms; phenyl; methylenedioxybenzyl; indanyl; naphthylmethyl; furfuryl; mono- or disubstituted phenyl, where the substituents, which may be identical to or different from each other, are each hydroxyl, nitro, amino, trifluoromethyl, alkyl of 1 to 3 carbon atoms, alkoxy of 1 to 3 carbon atoms or halogen; or mono- or disubstituted benzyl, where the substituents, which may be identical to or different from each other and are attached to the phenyl ring, are each hydroxyl, nitro, amino, trifluoromethyl, alkyl of 1 to 3 carbon atoms, alkoxy of 1 to 3 carbon atoms or halogen;

$R_6$ and $R_7$, which may be identical to or different from each other, are each hydrogen, alkyl of 1 to 8 carbon atoms; hydroxy-(alkyl of 1 to 4 carbon atoms); (alkoxy of 1 to 3 carbon atoms)-(alkyl of 1 to 4 carbon atoms); phenyl-(alkyl of 1 to 4 carbon atoms), where the phenyl moiety may be mono- or di-substituted and the substituents, which may be identical to or different from each other, are each alkyl of 1 to 3 carbon atoms, alkoxy of 1 to 3 carbon atoms, trifluoromethyl, fluorine, chlorine, bromine or methylenedioxy; unsubstituted mono- or di-substituted phenyl, where the substituents, which may be identical to or different from each other, are each alkyl of 1 to 3 carbon atoms, alkoxy of 1 to 3 carbon atoms, trifluoromethyl, fluorine, chlorine, bromine or methylenedioxy; cycloalkyl of 5 to 7 carbon atoms; pyridyl; picolyl; or furfuryl; or $R_6$ and $R_7$ together with the nitrogen atom to which they are attached represent an alkylenimino group with 4 to 6 carbon atoms, a thiomorpholino or thiomorpholino-1-oxide group;

and non-toxic, pharmacologically acceptable acid addition salts thereof.

The following are examples of specific embodiments of $R_1$, $R_2$ and $R_3$:

$R_1$: Methoxy, ethoxy, propoxy, isopropoxy, 2-hydroxyethoxy, 2-hydroxypropoxy, 3-hydroxypropoxy, 2-methoxycarbonylethoxy, 3-ethoxycarbonylpropoxy, 2-propoxycarbonylethoxy, 2-dimethylaminoethoxy, 3-dimethylaminopropoxy, 2-dimethylaminopropoxy, 2-diethylaminoethoxy, 3-diethylaminopropoxy, 3-dipropylaminopropoxy, 3-diisopropylaminopropoxy, 2-ethylpropylaminoethoxy, benzyloxy, 2-phenylethoxy, 2-methylmercapto-phenylethoxy, 3-phenylpropoxy, mercapto, methylmercapto, ethylmercapto, propylmercapto, isopropylmercapto, n-butylmercapto, sec. butylmercapto, isobutylmercapto, tert. butylmercapto, n-pentylmercapto, isopentylmercapto, tert. pentylmercapto, n-hexylmercapto, n-heptylmercapto, n-octylmercapto, 2-hydroxyethylmercapto, 3-hydroxypropylmercapto, 2-hydroxypropylmercapto, methoxycarbonylmethylmercapto, 2-methoxycarbonylethylmercapto, 3-methoxycarbonylpropylmercapto, ethoxycarbonylmethylmercapto, 2-propoxycarbonylethylmercapto, 2-dimethylaminoethylmercapto, 2-diethylaminoethylmercapto, 3-diethylaminopropylmercapto, 3-dipropylaminopropylmercapto, 1-phenylethylmercapto, 2-phenylethylmercapto, 3-phenylpropylmercapto, 1-(methylmercaptophenyl)ethylmercapto, 2-(methylmercaptophenyl)-ethylmercapto, 3-(methylmercaptophenyl)-propylmercapto, cyclopentylmercapto, cyclohexylmercapto, cycloheptylmercapto, phenylmercapto, hydroxyphenylmercapto, methylphenylmercapto, ethylphenylmercapto, isopropylphenylmercapto, methoxyphenylmercapto, ethoxyphenylmercapto, propoxyphenylmercapto, trifluoromethylphenylmercapto, aminophenylmercapto, fluorophenylmercapto, chlorophenylmercapto, bromophenylmercapto, dihydroxyphenylmercapto, dimethylphenylmercapto, dimethoxyphenylmercapto, difluorophenylmercapto, dichlorophenylmercapto, dibromophenylmercapto, difluorophenylmercapto, dichlorophenylmercapto, dibromophenylmercapto, methylmethoxyphenylmercapto, fluoromethoxyphenylmercapto, chloromethoxyphenylmercapto, bromomethoxyphenylmercapto, chloro-bromophenylmercapto, benzylmercapto, hydroxybenzylmercapto, methylbenzylmercapto, ethylbenzylmercapto, propylbenzylmercapto, methoxybenzylmercapto, ethoxybenzylmercapto, isopropyloxybenzylmercapto, methylenedioxy benzylmercapto, trifluoromethylbenzylmercapto, nitrobenzylmercapto, aminobenzylmercapto, fluorobenzylmercapto, chlorobenzylmercapto, bromobenzylmercapto, dimethylbenzylmercapto, dimethoxybenzylmercapto, dihydroxybenzylmercapto, difluorobenzylmercapto, dichlorobenzylmercapto, dibromobenzylmercapto, methyl-methoxybenzylmercapto, fluoromethoxybenzylmercapto, chloro-methoxybenzylmercapto, bromo-methoxybenzylmercapto, 2-indanylmercapto, 1-naphthylmethylmercapto, furfurylmercapto, amino, methylamino, ethylamino, propylamino, isopropylamino, butylamino, isobutylamino, tert. butylamino, pentylamino, isopentylamino tert. pentylamino, hexylamino, heptylamino, oxtylamino, cyclopentylamino, cyclohexylamino, cycloheptylamino, hydroxyethylamino, 3-hydroxypropylamino, 2-hydroxypropylamino, 4-hydroxybutylamino, 5-hydroxypentylamino, 8-hydroxyoctylamino, benzylamino, fluorobenzylamino, chlorobenzylamino, bromobenzylamino, methylbenzylamino, methoxybenzylbenzylamino, difluorobenzylamino, dichlorobenzylamino, dibromobenzylamino, dimethoxybenzylamino, methylenedioxy benzylamino, bromo-chlorobenzylamino, bromomethoxybenzylamino, 1-phenylethylamino, 2-phenylethylamino, 2-dimethoxyphenyl-ethylamino, 1-phenylpropylamino, 3-phenylpropylamino, 2-phenylbutylamino, 4-phenyl-butylamino, phenylamino, methoxyphenylamino, ethoxyphenylamino, trifluorophenylamino, pyridylamino, picolylamino, furfurylamino, N-methyl-phenylamino, N-methylpyridylamino, N-methyl-picolylamino, N-methylbenzylamino, N-ethyl-benzylamino, N-propyl-benzylamino, N-isopropyl-benzylamino, N-butyl-benzylamino, N-pentylbenzylamino, N-octyl-benzylamino, N-hydroxyethylbenzylamino, N-hydroxypropyl-benzylamino, N-hydroxybutyl-benzylamino, N-methyl-2-(dimethoxyphenyl)-ethylamino, dimethylamino, diethylamino, dipropylamino, diisopropylamino, dibutylamino, dipentylamino, dihexylamino, diheptylamino, methyl-ethylamino, methylpropylamino, ethyl-propylamino, ethyl-isopropylamino, diethanolamino, N-hydroxyethyl-methoxyethylamino, dihydroxypropylamino, pyrrolidino, piperidino, hexamethyleneimino, thiomorpholino, thiomorpholino-1-oxide, morpholino, methylmorpholino or dimethylmorpholino;

$R_2$: Morpholino, methylmorpholino, dimethylmorpholino, thiomorpholino, methyl-thiomorpholino, thiomorpholino-1-oxide, dimethylthiomorpholino-1-oxide or thiomorpholino-1,1-dioxide; and $R_3$: Hydrogen, methyl, ethyl, n-propyl, isopropyl, n-butyl, sec. butyl, isobutyl, tert. butyl, n-pentyl, isopentyl, neopentyl, tert. pentyl, phenyl, benzyl, 1-phenylethyl, 1-phenylpropyl, 2-phenylethyl, 2-phenylpropyl, 3-phenylpropyl, hydroxyethyl, hydroxypropyl, hydroxyisopropyl, hydroxybutyl, formyl, acetyl, propionyl, butanoyl, methoxyacetyl, methoxypropionyl, aceto-acetyl, hydroxycarbonylacetyl, hydroxycarbonylpropionyl, hydroxycarbonyl-butanoyl, pyridinoyl-(2), pyridinoyl-(3), pyridinoyl-(4), furoyl-(2), thenoyl-(2), 2-acetoxybenzoyl, 3-acetoxybenzoyl or 4-acetoxybenzoyl.

A preferred sub-genus is constituted by those compounds of the formula I
wherein $R_1$ is methoxy; benzyloxy; ethoxy; hydroxy-ethoxy; diethylamino-ethoxy; mercapto; (alkyl of 1 to 8 carbon atoms)mercapto; cyclohexylmercapto; phenylethylmercapto; phenylpropyl-mercapto; methylmercaptophenethyl—mercapto; hydroxyethylmercapto; diethylaminoethyl-mercapto; methoxycarbonylmethyl-mercapto; 1-naphthylmethylmercapto; furfurylmercapto; 2-indanyl-mercapto; unsubstituted or mono-substituted phenylmercapto, where the substituent is fluorine, chlorine, bromine, methyl, hydroxyl, methoxy or amino; unsubstituted or monosubstituted benzylmercapto, where the substituent is attached to the phenyl moiety and is fluorine, chlorine, methyl, hydroxyl, methoxy, nitro or trifluoromethyl; dichlorobenzyl-mercapto; methylenedioxybenzylmercapto; dimethoxybenzyl-mercapto; piperidino; thiomorpholino; thiomorpholino-1-oxide; amino; (unsubstituted or monosubstituted alkyl of 1 to 4 carbon atoms)-amino, where the substituent is hydroxyl or methoxy; N,N-di-(unsubstituted or monosubstituted alkyl of 1 to 4 carbon atoms)-amino, where the substituent is hydroxyl or methoxy; (unsubstituted, mono- or disubstituted phenyl)-(unsubstituted or monosubstituted alkyl of 1 to 4 carbon atoms)- amino, where the substituents on the phenyl moiety are each methyl, methoxy, ethoxy, trifluoromethyl, fluorine, chlorine or methylenedioxy, and the substituent on the alkyl moiety is hydroxyl or methoxy; N-(unsubstituted or monosubstituted alkyl of 1 to 4 carbon atoms)-(unsubstituted, mono- or disubstituted phenyl)-(unsubstituted or monosubstituted alkyl of 1 to 4 carbon atoms)-amino, where the substituent on each alkyl moiety is hydroxyl or methoxy and the substituent on the phenyl moiety are each methyl, methoxy, ethoxy, trifluoromethyl, fluorine, chlorine or methylenedioxy; (unsubstituted mono- or disubstituted phenyl)-amino, where the substituents on the phenyl moiety are each methyl, methoxy, ethoxy, trifluoromethyl, fluorine, chlorine or methylenedioxy; N-(unsubstituted or monosubstituted alkyl of 1 to 4 carbon atoms)-(unsubstituted, mono or disubstituted phenyl)-amino, where the substituent on the alkyl moiety is hydroxyl or methoxy, and the substituents on the phenyl moiety are each methyl, methoxy, ethoxy, trifluoromethyl, fluorine, chlorine or methylenedioxy; alkyl of 5 to 8 carbon atoms; cyclohexylamino, picolylamino; N-methylpicolylamino; or furfurylamino;

$R_2$ is thiomorpholino, thiomorpholino-1-oxide or thiomorpholino-1-dioxide;

one of $R_1$ and $R_2$ is morpholino, 2-methylmorpholino or 2,6-dimethyl-morpholino and the other has the respective meanings defined above;

$R_3$ is hydrogen; alkyl of 1 to 5 carbon atoms; hydroxy-(alkyl of 1 to 5 carbon atoms); acetyl; methoxyacetyl; acetyl-acetyl; alkanoyl of 2 to 4 carbon atoms; carboxy-(alkanoyl of 2 to 4 carbon atoms); formyl, 2-acetoxybenzoyl; nicotinoyl; 2-furoyl; or 2-thenoyl; and n is 2 or 3;

and non-toxic, pharmacologically acceptable acid addition salts thereof.

An especially preferred sub-genus is constituted by those compounds of the formula I
wherein $R_1$ is benzyloxy; methoxy; 2-hydroxy-ethoxy; phenylmercapto; (alkyl of 1 to 2 carbon atoms)-mercapto; hydroxy-(alkyl of 1 to 2 carbon atoms)-mercapto; diethylamino-(alkyl of 1 to 2 carbon atoms)-mercapto; (unsubstituted, mono- or disubstituted phenyl)-(alkyl of 1 to 2 carbon atoms)-mercapto, where the substituents are each fluorine, chlorine or methoxy; (unsubstituted, mono- or disubstituted phenyl)-amino, where the substituents on the phenyl moiety are each methyl, methoxy, ethoxy, trifluoromethyl, fluorine, chlorine or methylenedioxy; (unsubstituted, mono- or disubstituted phenyl)-(unsubstituted or monosubstituted alkyl of 1 to 3 carbon atoms)-amino, where the substituents on the phenyl moiety are each methyl, methoxy, ethoxy, trifluoromethyl, fluorine, chlorine or methylenedioxy, and the substituent on the alkyl moiety is hydroxyl; or N-(unsubstituted or monosubstituted alkyl of 1 to 3 carbon atoms)-(unsubstituted, mono- or disubstituted phenyl)-(unsubstituted or monosubstituted alkyl of 1 to 3 carbon atoms)-amino, where the substituent on each alkyl moiety is hydroxyl, and the substituents on the phenyl moiety are each methyl, methoxy, ethoxy, trifluoromethyl, fluorine, chlorine or methylenedioxy;

$R_3$ is hydrogen, methyl, 2-hydroxy-ethyl, formyl or 2-furoyl; and n is 2;

and non-toxic, pharmacologically acceptable acid addition salts thereof.

The compounds embraced by formula I may be prepared by the following methods:

METHOD A

By reacting a pyrimido[5,4-d]pyrimidine of the formula

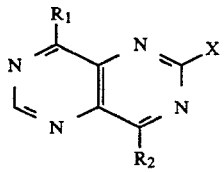

wherein $R_1$ and $R_2$ have the same meanings as in formula I, and

X is a nucleophilic exchangeable group, with a perhydro-1,4-diazine of the formula

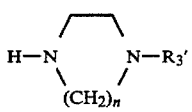

wherein n has the same meanings as in formula I, and $R_3'$ is an easily removable protective group or has the meanings defined for $R_3$ in formula I followed by removal of the protective group.

Examples of nucleophilic exchangeable groups are halogen, such as chlorine or bromine; substituted hydroxyl groups, such as phenoxy, or a sulfonyl group, such as methylsulfonyl. Examples of easily removable protective groups are trimethylsilyl; a carbonic ester radical, such as carbethoxy; or alkanoyl, such as formyl.

The reaction is advantageously carried out in an inert solvent such as acetone, methyl ethyl ketone, tetrahydrofuran, dioxane, chlorobenzene, dimethylformamide, or dimethylsulfoxide, optionally in the presence of an inorganic base such as sodium carbonate or potassium hydroxide, or a tertiary organic base such as trimethylamine or pyridine, where the latter may simultaneously also serve as the solvent, and optionally in the presence of a reaction accelerator such as a copper salt, at temperatures between 20° and 150° C., but preferably between 30° and 100° C. However, the reaction may also be carried out without a solvent or in an excess of the compound of the formula III.

The subsequent removal of the protective group is advantageously carried out by hydrolysis in the presence of an acid or a base in an aqueous solvent, such as water/methanol or water/ethanol, and preferably at the boiling point of the reaction mixture.

METHOD B

For the preparation of a compound of the formula I wherein $R_1$ is $-OR_4$ or $-SR_5$, by reacting a pyrimido[5,4-d]pyrimidine of the formula

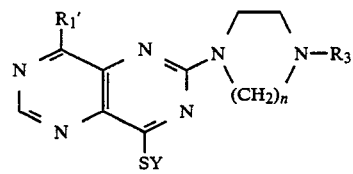

wherein $R_3$ and n have the same meanings as in formula I, $R_1$ is $-OR_4$ or $-SR_5$, where $R_4$ and $R_5$ have the meanings previously defined, and Y is lower alkyl or aralkyl, such as methyl, ethyl, propyl, benzyl, methylbenzyl, chlorobenzyl, nitrobenzyl, or naphthylmethyl with an amine of the formula

H—$R_2$ (V)

wherein $R_2$ has the same meanings as in formula I.

The reaction is advantageously carried out in a solvent, such as acetone, chloroform, benzene, tetrahydrofuran, dimethylformamide, ethanol or isopropanol, or in excess of the amine of the formula V, at temperatures between 20° and 100° C., but preferably between 40° and 80° C. The reaction can, however, also be carried out without a solvent.

METHOD C

For the preparation of a compound of the formula I wherein $R_1$ is

wherein $R_6$ and $R_7$ are other than both hydrogen at the same time.

By reacting a pyrimido[5,4-d]pyrimidine of the formula

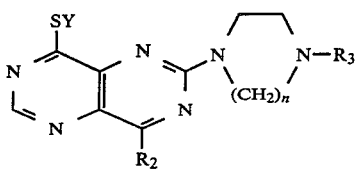

wherein
R$_2$, R$_3$ and n have the same meanings as in formula I, and
Y is lower alkyl or aralkyl such as methyl, ethyl, propyl, benzyl, methylbenzyl, chlorobenzyl, nitrobenzyl or naphthylmethyl,
with an amine of the formula

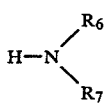

wherein R$_6$ and R$_7$ have the same meanings as in formula I, except both hydrogen at the same time.

The reaction is advantageously carried out in a solvent, such as acetone, chloroform, benzene, tetrahydrofuran, dimethylformamide, ethanol or isopropanol or in an excess of the amine of the formula VII and optionally in a closed vessel, at temperatures between 100° and 200° C., but preferably between 130° and 180° C. The reaction can, however, also be carried out without a solvent.

METHOD D

For the preparation of a compound of the formula I, wherein R$_1$ is —SR$_5$ or

wherein R$_5$ and R$_6$ are other than hydrogen and

is other than cyclic amino.

By reacting a pyrimido[5,4-d]pyrimidine of the formula

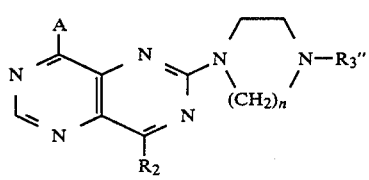

wherein
R$_2$ and n have the same meanings as in formula I,
R$_3$ is an easily removable protective group or has the meanings defined for R$_3$ in formula I with the exception of hydrogen, and A is mercapto or —NH—R$_7$, where R$_7$ has the meanings previously defined, with a compound of the formula $$Z—R_1'' \quad (IX)$$

wherein
Z is a nucleophilic exchangeable group, such as halogen or a sulfonic acid ester radical, and
R'' has the meanings defined for R$_5$ and R$_6$ in formula I, with the exception of hydrogen, phenyl optionally mono- or disubstituted by hydroxy, nitro, amino, trifluoromethyl, alkyl, alkoxy groups and/or halogen atoms, or phenyl substituted by a methylenedioxy group, followed by removal of the protective radical.

Examples of nucleophilic exchangeable groups are chlorine, bromine, iodine, methylsulfonyloxy, methylsulfonyloxy or p-toluene-sulfonyloxy, and examples of easily removable protective radicals are trimethylsilyl, a carbonic acid ester radical such as carbethoxy, or alkanoyl such as formyl.

The reaction is advantageously carried out in a solvent, such as acetone, methyl ethyl ketone, methylene chloride, chloroform, tetra-ydrofuran, dioxane, dimethylformamide or dimethyl sulfoxide, optionally in the presence of a base, such as sodium carbonate, sodium hydroxide, potassium hydroxide, potassium tert.butylate, triethylamine or pyridine, where the latter may simultaneously also serve as a solvent, and optionally in the presence of a reaction accelerator such as an alkali metal iodide, for instance potassium iodide, at temperatures between 0° and 100° C., but preferably between 20° and 80° C. The reaction can, however, also be carried out without a solvent or in an excess of the compound of the formula IX.

The subsequent removal of the protective group is advantageously carried out by hydrolysis in the presence of an acid or a base, in an aqueous solvent such as water/methanol or water/ethanol, and preferably at the boiling point of the reaction mixture.

If methods A to D yield a compound of the formula I, wherein R$_3$ is alkanoyl of 2 to 4 carbon atoms optionally substituted by methoxy, acetyl or carboxyl, a formyl, acetoxy-benzoyl, pyridinoyl, furoyl or thenoyl group, this compound can be converted by means of hydrolysis into the corresponding compound of the formula I wherein R$_3$ is hydrogen.

If a compound of the formula I is obtained, wherein R$_3$ is hydrogen, this compound can be converted by means of acylation into a corresponding compound of the formula I wherein R$_3$ is alkanoyl of 2 to 4 carbon atoms optionally substituted by methoxy, acetyl, carboxyl, formyl, acetoxybenzoyl, pyridinoyl, furoyl or thenoyl.

If a compound of the formula I is obtained, wherein R$_1$ is thiomorpholino and/or R$_2$ is thiomorpholino optionally substituted by 1 or 2 methyl groups, this compound may be converted by means of oxydation into a corresponding thiomorpholino-1-oxide compound of the formula I. If a compound of the formula I is obtained, wherein R$_2$ is thiomorpholino or thiomorpholino-1-oxide optionally substituted by 1 or 2 methyl groups, this compound may be converted by means of oxidation into a corresponding thiomorpholino-1,1-dioxide compound of the formula I.

The hydrolysis is advantageously carried out in an aqueous solvent, such as water, water/ethanol, water/isopropanol or water/dioxane, in the presence of an acid such as hydrochloric acid or sulfuric acid or a base such as sodium hydroxide or potassium hydroxide, at elevated temperatures, preferably at the boiling point of the reaction mixture.

The acylation is advantageously carried out in a solvent, such as dimethylformamide, tetrahydrofuran, dioxane, methylene chloride, chloroform or toluene, with a corresponding carboxylic acid or a reactive derivative thereof, such as an anhydride, acid halogenide, ketene, 1-imidazolyl derivative or a mixed anhydride with carboxylic acids or carbonic acid esters, optionally in the presence of an acid-activating and/or dehydrating agent, such as ethyl chloroformate, thionyl chloride, N,N'-dicyclohexylcarbodiimide or N,N'-carbonyldiimidazole, and optionally in the presence of an inorganic base such as sodium carbonate, or a tertiary organic base such as triethylamine or pyridine, which may simultaneously serve as a solvent, at temperatures between $-25°$ and $120°$ C., but preferably between $0°$ and $50°$ C. The formylation is particularly advantageously carried out with chloral.

The oxidation is preferably carried out in a solvent, such as water, water/pyridine, glacial acetic acid or methanol, and, depending on the particular oxidizing agent, at temperatures between $-80°$ and $100°$ C.

For the preparation of a thiomorpholino-1-oxide of the formula I, the oxidation is advantageously carried out with an equimolar amount of the oxidizing agent, for example with hydrogen peroxide in glacial acetic acid at $0°$ to $20°$ C., with a peracid such as peracetic acid, m-chloroperbenzoic acid or peroxy-trifluoroacetic acid at $0°$ to $50°$ C., with potassium permanganate in dilute hydrochloric acid at $0°$ C., with sodium metaperiodate in aqueous methanol or ethanol at $15°$ to $25°$ C., with tert.butyl hypochlorite in methanol at $-80°$ to $-30°$ C., with iodobenzene dichloride in aqueous pyridine at $0°$ to $50°$ C., with nitric acid in glacial acetic acid at $0°$ to $20°$ C. or with chromic acid in glacial acetic acid or acetone at $0°$ to $20°$ C.

For the preparation of a thiomorpholino-1,1-dioxide of the formula I, the oxidation is advantageously carried out with two equivalents of the corresponding oxidizing agent starting from a thiomorpholino compound of the formula I, or with one molar equivalent starting from a thiomorpholino-1-oxide compound of the formula I analogous to the method described above. However, the reaction is carried out at a temperature higher by $10°$ to $50°$ C.

The compounds embraced by formula I are basic and therefore form addition salts with inorganic or organic acids. Examples of non-toxic, pharmacologically acceptable acid addition salts are those formed with hydrochloric acid, hydrobromic acid, sulfuric acid, phosphoric acid, methanesulfonic acid, p-toluenesulfonic acid, acetic acid, lactic acid, citric acid, tartaric acid, succinic acid, maleic acid, fumaric acid, salicylic acid or the like.

The starting compounds of the formulas II, IV and VI may be obtained by stepwisely replacing the chlorine atoms of 2,4,8-trichloro-pyrimido[5,4-d]pyrimidine (see German Pat. No. 1,116,676). The starting compounds of the formulas II, IV and VI are described in the examples below, and the starting compounds of the formulas III, V, VII and IX are known from the literature or can be obtained by known methods.

The starting compound of the formula VIII are obtained by reaction of a corresponding compound according to method A.

The following examples illustrate the present invention and will enable others skilled in the art to understood it more completely. It should be understood, however, that the invention is not limited solely to the particular examples given below.

The melting points given in the examples are uncorrected melting points.

PREPARATION OF STARTING COMPOUNDS

Example A 2,8-Dichloro-4-morpholino-pyrimido[5,4-d]pyrimidine 118 gm (0.5 mol) of 2,4,8-trichloro-pyrimido[5,4-d]pyrimidine were suspended in 1.2 liters of acetone, and a solution of 44 ml (0.5 mol) of morpholine and 70 ml (0.5 mol) of triethylamine in 100 ml of acetone was slowly added to the suspension while stirring at room temperature. After stirring the resulting mixture for about 30 minutes, 1.3 liters of water were added to the reaction mixture, whereby the precipitated triethylamine hydrochloride went into solution and the reaction product was precipitated. After standing for a while, the reaction product was suction-filtered off, washed thoroughly with water and then with a little methanol, and dried at $60°$ C.

Yield: 132 gm (92% of theory); m.p.: $179°-181°$ C.

M.p.: $183°-185°$ C. (from ethanol).

The reaction can also be carried out in analogous manner by using an aqueous potassium carbonate solution instead of triethylamine.

The following compounds were prepared in analogous manner:

2,8-Dichloro-4-(2-methylmorpholino)-pyrimido[5,4-d]pyrimidine M.p.: $129°-131°$ C.;

2,8-Dichloro-4-(2,6-dimethylmorpholino)-pyrimido[5,4-d]pyrimidine M.p.: $181°-183°$ C.;

2,8-Dichloro-4-thiomorpholino-pyrimido[5,4-d]pyrimidine M.p.: $154°-157°$ C.;

2,8-Dichloro-4-(1-oxido-thiomorpholino)-pyrimido[5,4-d]pyrimidine M.p.: $195°-198°$ C. (dioxane); and 2,8-Dichloro-4-(1,1-dioxido-thiomorpholino)-pyrimido[5,4-d]-pyrimidine M.p.: $270°-273°$ C. (decomp., dioxane).

Example B

8-Benzylthio-2-chloro-4-morpholino-pyrimido[5,4-d]-pyrimidine

A solution of 28 gm (0.52 mol) of sodium methylate in 150 ml of methanol and 59 ml (0.5 mol) of benzyl mercaptane was slowly added, while stirring, to a suspension of 143 gm (0.5 mol) of 2,8-dichloro-4-morpholino-pyrimido[5,4-d]pyrimidine in 2 liters of acetone. After stirring the reaction mixture for about one hour, about 2 liters of water were added, whereby the precipitated sodium chloride went into solution and further reaction product was precipitated. After standing for a while, the reaction product was suction-filtered off, washed with about 1 liter of water and then with about 500 ml of methanol, and dried at $60°$ C.

Yield: 182 gm (97% of theory); m.p.: $157°-159°$ C.

M.p.: $159°-161°$ C. (from isopropanol).

The reaction can also be carried out in analogous manner by using 2N sodium hydroxide instead of the sodium methylate solution.

The following compounds were prepared in analogous manner:

2-Chloro-8-methylthio-4-morpholino-pyrimido-[5,4-d]pyrimidine M.p.: 179°–180° C.;

2-Chloro-8-methylthio-4-thiomorpholino-pyrimido-[5,4-d]pyrimidine M.p.: 165°–167° C.;

2-Chloro-8-methylthio-4-(1-oxido-thiomorpholino)-pyrimido-[5,4-d]-pyrimidine M.p. 260°–262° C.;

8-Ethylthio-2-chloro-4-thiomorpholino-pyrimido-[5,4-d]-pyrimidine M.p.: 134°–146° C.;

8-Ethylthio-2-chloro-4-(1-oxido-thiomorpholino)-pyrimido-[5,4-d]-pyrimidine M.p.: 197°–199° C.;

2-Chloro-4-morpholino-8-propylthio-pyrimido-[5,4-d]-pyrimidine M.p.: 126°–128° C.;

2-Chloro-8-isopropylthio-4-morpholino-pyrimido-[5,4-d]-pyrimidine M.p.: 132°–134° C.;

8-Butylthio-2-chloro-4-morpholino-pyrimido-[5,4-d]-pyrimidine M.p.: 132°–133° C.;

2-Chloro-4-morpholino-8-pentylthio-pyrimido-[5,4-d]-pyrimidine M.p.: 84°–87° C.;

2-Chloro-4-morpholino-8-octylthio-pyrimido-[5,4-d]-pyrimidine M.p.: 66°–69° C.;

2-Chloro-8-cyclohexylthio-4-morpholino-pyrimido-[5,4-d]-pyrimidine M.p.: 179°–181° C.;

2-Chloro-4-morpholino-8-phenylthio-pyrimido-[5,4-d]-pyrimidine M.p.: 196°–197° C.;

2-Chloro-8-phenylthio-4-thiomorpholino-pyrimido-[5,4-d]-pyrimidine M.p.: 236°–238° C.;

2-Chloro-4-(1-oxido-thiomorpholino)-8-phenylthio-pyrimido-[5,4-d]-pyrimidine M.p.: 253°–255° C.;

8-Benzylthio-2-chloro-4-thiomorpholino-pyrimido-[5,4-d]-pyrimidine M.p.: 162°–164° C.;

8-Benzylthio-2-chloro-4-(1-oxido-thiomorpholino)-pyrimido-[5,4-d]-pyrimidine M.p.: 188°–190° C.;

8-Benzylthio-2-chloro-4-(1,1-dioxido-thiomorpholino)-pyrimido-[5,4-d]-pyrimidine M.p.: 238°–239° C.;

2-Chloro-4-morpholino-8-phenethylthio-pyrimido-[5,4-d]-pyrimidine M.p.: 148°–150° C.;

2-Chloro-8-phenethylthio-4-thiomorpholino-pyrimido-[5,4-d]-pyrimidine M.p. 155°–157° C.;

2-Chloro-4-(1-oxido-thiomorpholino)-8-phenethylthio-pyrimido-[5,4-d]-pyrimidine M.p.: 248°–250° C.;

2-Chloro-4-morpholino-8-(3-phenylpropylthio)-pyrimido-[5,4-d]-pyrimidine M.p.: 127°–129° C.;

8-Benzylthio-2-chloro-4-(2-methylmorpholino)-pyrimido-[5,4-d]-pyrimidine M.p.: 40°–60° C.;

8-Benzylthio-2-chloro-4-(2,6-dimethylmorpholino)-pyrimido-[5,4-d]-pyrimidine M.p.: 85°–90° C.;

2-Chloro-8-(methoxycarbonyl-methylthio)-4-morpholino-pyrimido-[5,4-d]-pyrimidine M.p.: 188°–190° C.;

2-Chloro-8-(2-diethylamino-ethylthio)-4-morpholino-pyrimido-[5,4-d]-pyrimidine Resin;

2-Chloro-8-(2-diethylamino-ethylthio)-4-(1-oxido-thiomorpholino)-pyrimido-[5,4-d]-pyrimidine M.p.: 95°–99° C.;

2-Chloro-8-(2-hydroxyethylthio)-4-(1-oxido-thiomorpholino)-pyrimido-[5,4-d]-pyrimidine M.p.: 228°–230° C. (decomp.);

2-Chloro-8-(4-methoxybenzylthio)-4-morpholino-pyrimido-[5,4-d]-pyrimidine M.p.: 173°–174° C.;

2-Chloro-8-(3,4-dimethoxybenzylthio)-4-morpholino-pyrimido-[5,4-d]-pyrimidine M.p.: 143°–145° C.;

2-Chloro-8-(4-methylbenzylthio)-4-morpholino-pyrimido-[5,4-d]-pyrimidine M.p.: 177°–179° C.;

2-Chloro-8-(4-fluorobenzylthio)-4-morpholino-pyrimido-[5,4-d]-pyrimidine M.p.: 163°–165° C.;

2-Chloro-8-(4-chlorobenzylthio)-4-morpholino-pyrimido-[5,4-d]-pyrimidine M.p.: 135°–145° C.;

2-Chloro-8-(2,4-dichlorobenzylthio)-4-morpholino-pyrimido-[5,4-d]-pyrimidine M.p.: 175°–177° C.;

2-Chloro-8-(4-hydroxyphenylthio)-4-morpholino-pyrimido-[5,4-d]-pyrimidine M.p.: >300° C.;

2-Chloro-8-methoxy-4-morpholino-pyrimido[5,4-d]-pyrimidine M.p.: 160°–162° C.;

2-Chloro-8-methoxy-4-(1-oxido-thiomorpholino)-pyrimido-[5,4-d]-pyrimidine M.p.: 218°–221° C.;

8-Ethoxy-2-chloro-4-morpholino-pyrimido-[5,4-d]-pyrimidine M.p.: 153°–155° C.;

2-Chloro-8-(2-hydroxyethoxy)-4-morpholino-pyrimido-[5,4-d]-pyrimidine M.p.: 190°–195° C.;

2-Chloro-4-morpholino-8-(4-tolylthio)-pyrimido-[5,4-d]-pyrimidine M.p.: 163°–165° C.;

2-Chloro-8-(4-methoxyphenylthio)-4-morpholino-pyrimido-[5,4-d]-pyrimidine M.p.: 196°–199° C.;

8-(2-Aminophenylthio)-2-chloro-4-morpholino-pyrimido-[5,4-d]-pyrimidine M.p.: 151°–153° C.;

2-Chloro-8-(4-chlorophenylthio)-4-morpholino-pyrimido-[5,4-d]-pyrimidine M.p.: 208°–210° C.;

2-Chloro-8-(4-fluorophenylthio)-4-morpholino-pyrimido-[5,4-d]-pyrimidine M.p.: 213°–215° C.;

8-(4-Bromophenylthio)-2-chloro-4-morpholino-pyrimido-[5,4-d]-pyrimidine M.p.: 205°–207° C.;

8-(4-Bromophenylthio)-2-chloro-4-(1-oxido-thiomorpholino)-pyrimido-[5,4-d]-pyrimidine M.p.: 272°–275° C.;

2-Chloro-8-(4-chlorophenylthio)-4-(1-oxido-thiomorpholino)-pyrimido-[5,4-d]-pyrimidine M.p.: 267°–269° C.;

2-Chloro-8-(4-hydroxyphenylthio)-4-(1-oxido-thiomorpholino)-pyrimido-[5,4-d]-pyrimidine M.p.: >280° C.;

2-Chloro-8-(4-methoxyphenylthio)-4-(1-oxido-thiomorpholino)-pyrimido-[5,4-d]-pyrimidine M.p.: 239°–241° C.;

2-Chloro-4-(1-oxido-thiomorpholino)-8-(4-tolylthio)-pyrimido-[5,4-d]-pyrimidine M.p.: 261°–263° C.;

2-Chloro-8-(2-fluorobenzylthio)-4-morpholino-pyrimido-[5,4-d]-pyrimidine M.p.: 151°–153° C.;

2-Chloro-8-(3-fluorobenzylthio)-4-morpholino-pyrimido-[5,4-d]-pyrimidine M.p.: 192°–194° C.;

2-Chloro-8-(2-fluorobenzylthio)-4-(1-oxido-thiomorpholino)-pyrimido-[5,4-d]-pyrimidine M.p.: 206°–208° C.;

2-Chloro-8-(3-fluorobenzylthio)-4-(1-oxido-thiomorpholino)-pyrimido-[5,4-d]-pyrimidine M.p.: 205°–207° C.;

2-Chloro-8-(2-chlorobenzylthio)-4-morpholino-pyrimido-[5,4-d]-pyrimidine M.p.: 178°–180° C.;

2-Chloro-8-(2-chlorobenzylthio)-4-(1-oxido-thiomorpholino)-pyrimido-[5,4-d]-pyrimidine M.p.: 203°–206° C.;

2-Chloro-8-(4-chlorobenzylthio)-4-(1-oxido-thiomorpholino)-pyrimido-[5,4-d]-pyrimidine M.p.: 232°–234° C.;

2-Chloro-8-(3,4-dichlorobenzylthio)-4-morpholino-pyrimido-[5,4-d]-pyrimidine M.p.: 153°–156° C.;

2-Chloro-8-(3,4-dichlorobenzylthio)-4-(1-oxido-thiomorpholino)-pyrimido-[5,4-d]-pyrimidine M.p.: 210°–212° C.;

2-Chloro-8-(2,4-dichlorobenzylthio)-4-(1-oxido-thiomorpholino)-pyrimido-[5,4-d]-pyrimidine M.p.: 227°–229° C.;

2-Chloro-4-morpholino-8-(3-trifluoromethylbenzylthio)-pyrimido-[5,4-d]-pyrimidine M.p.: 127°–129° C.;

2-Chloro-4-(1-oxido-thiomorpholino)-8-(3-trifluoromethyl-benzylthio)-pyrimido-[5,4-d]-pyrimidine M.p.: 211°–213° C.;

2-Chloro-8-(4-methylbenzylthio)-4-(1-oxido-thiomorpholino)-pyrimido-[5,4-d]-pyrimidine M.p.: 263°–264° C.;

2-Chloro-8-(4-methoxybenzylthio)-4-(1-oxido-thiomorpholino)-pyrimido-[5,4-d]-pyrimidine M.p.: 217°–219° C.;

2-Chloro-8-mercapto-4-morpholino-pyrimido-[5,4-d]-pyrimidine M.p.: >300° C. (decomp.);

2-Chloro-8-(2-indanylthio)-4-morpholino-pyrimido-[5,4-d]-pyrimidine M.p.: 202°–205° C.;

2-Chloro-8-(α-methyk-4-methylthio-benzylthio)-4-morpholino-pyrimido-[5,4-d]pyrimidine M.p.: 146°–149° C.;

2-Chloro-8-(α-methyl-4-methylthio-benzylthio)-4-(1-oxido-thiomorpholino)-pyrimido-[5,4-d]-pyrimidine M.p.: 200°–202° C.;

2-Chloro-4-(1-oxido-thiomorpholino)-8-propylthio-pyrimido-[5,4-d]-pyrimidine M.p.: 209°–210° C.;

2-Chloro-4-(1-oxido-thiomorpholino)-8-(3-phenylpropylthio)-pyrimido-[5,4-d]-pyrimidine M.p.: 172°–174° C.; and 2-Chloro-8-(2-hydroxyethoxy)-4-(1-oxido-thiomorpholino)-pyrimido-[5,4-d]-pyrimidine M.p.: 235°–236° C.

Example C 8-(N-Benzyl-methylamino)-2-chloro-4-(1-oxido-thiomorpholino)-pyrimido-[5,4-d]-pyrimidine A solution of 12.2 gm (0.1 mol) of N-benzyl-methylamine in 50 ml of dioxane was slowly poured, while stirring, to a suspension of 15.9 gm (0.05 mol) of 2,8-dichloro-4-(1-oxido-thiomorpholino)-pyrimido-[5,4-d]-pyrimidine in about 250 ml of dioxane, and the resulting mixture was heated at 30°–40° C. for about 30 minutes. After taking up the reaction mixture in about 1 liter of water, the reaction product was obtained as a pale yellow precipitate which, after some standing, was suction filtered off, washed with water and dried at about 60° C.

Yield: 18.6 gm (92% of theory).

After recrystallization from ethanol, the 8-(N-benzyl-methylamino)-2-chloro-4-(1-oxido-thiomorpholino)-pyrimido-[5,4-d]-pyrimidine melted at 158°–160° C.

The following compounds were prepared in analogous manner:

2-Chloro-8-diethanolamino-4-morpholino-pyrimido-[5,4-d]-pyrimidine M.p.: 129°–131° C.;

8-Amino-2-chloro-4-morpholino-pyrimido-[5,4-d]-pyrimidine M.p.: 206°–208° C.;

8-Amino-2-chloro-4-(1-oxido-thiomorpholino)-pyrimido-[5,4-d]-pyrimidine M.p.: 270°–272° C.;

2-Chloro-8-methylamino-4-(1-oxido-thiomorpholino)-pyrimido-[5,4-d]-pyrimidine M.p.: 278°–280° C.;

2-Chloro-4-(1-oxido-thiomorpholino)-8-propylamino-pyrimido-[5,4-d]-pyrimidine M.p.: 174°–176° C.;

2-Chloro-8-isopropylamino-4-(1-oxido-thiomorpholino)-pyrimido-[5,4-d]-pyrimidine M.p.: 210°–212° C.;

8-Butylamino-2-chloro-4-(1-oxido-thiomorpholino)-pyrimido-[5,4-d]-pyrimidine M.p.: 179°–181° C.;

2-Chloro-8-isoamylamino-4-(1-oxido-thiomorpholino)-pyrimido-[5,4-d]-pyrimidine M.p.: 176°–178° C.;

2-Chloro-8-octylamino-4-(1-oxido-thiomorpholino)-pyrimido-[5,4-d]-pyrimidine M.p.: 145°–147° C.;

2-Chloro-8-cyclohexylamino-4-(1-oxido-thiomorpholino)-pyrimido-[5,4-d]-pyrimidine M.p.: 207°–209° C.;

2-Chloro-8-diethylamino-4-(1-oxido-thiomorpholino)-pyrimido-[5,4-d]-pyrimidine M.p.: 184°–186° C.;

2-Chloro-8-dibutylamino-4-(1-oxido-thiomorpholino)-pyrimido-[5,4-d]-pyrimidine M.p.: 187°–189° C.;

2-Chloro-4-(1-oxido-thiomorpholino)-8-piperidino-pyrimido-[5,4-d]-pyrimidine M.p.: 203°–205° C.;

2-Chloro-4-(1-oxido-thiomorpholino)-8-thiomorpholino-pyrimido-[5,4-d]-pyrimidine M.p.: 229°–231° C.;

2-Chloro-8-morpholino-4-(1-oxido-thiomorpholino)-pyrimido-[5,4-d]-pyrimidine M.p.: 232°–233° C.;

8-Benzylamino-2-chloro-4-morpholino-pyrimido-[5,4-d]-pyrimidine M.p.: 139°–141° C.;

8-Benzylamino-2-chloro-4-thiomorpholino-pyrimido-[5,4-d]-pyrimidine M.p.: 94°–96° C.;

8-Benzylamino-2-chloro-4-(1-oxido-thiomorpholino)-pyrimido-[5,4-d]-pyrimidine M.p.: 232°–233° C.;

8-Benzylamino-2-chloro-4-(1,1-dioxido-thiomorpholino)-pyrimido-[5,4-d]-pyrimidine M.p.: 213°–215° C.;

2-Chloro-4-morpholino-8-phenethylamino-pyrimido-[5,4-d]-pyrimidine M.p.: 132°–134° C.;

2-Chloro-4-(1-oxido-thiomorpholino)-8-phenethylamino-pyrimido-[5,4-d]-pyrimidine M.p.: 198°–200° C.;

2-Chloro-4-(1-oxido-thiomorpholino)-8-(3-phenylpropylamino)-pyrimido-[5,4-d]-pyrimidine M.p.: 152°–154° C.;

2-Chloro-4-(1-oxido-thiomorpholino)-8-(D-1-phenylethylamino)-pyrimido-[5,4-d]-pyrimidine M.p.: 167°–169° C.;

2-Chloro-4-(1-oxido-thiomorpholino)-8-(L-1-phenylethylamino)-pyrimido-[5,4-d]-pyrimidine M.p.: 167°–169° C.;

8-(N-Benzyl-methylamino)-2-chloro-4-morpholino-pyrimido-[5,4-d]-pyrimidine M.p.: 121°–123° C.;

8-(N-Ethyl-benzylamino)-2-chloro-4-(1-oxido-thiomorpholino)-pyrimido-[5,4-d]-pyrimidine M.p.: 163°–165° C.;

8-(N-Benzyl-propylamino)-2-chloro-4-(1-oxido-thiomorpholino)-pyrimido-[5,4-d]-pyrimidine M.p.: 183°–184° C.;

8-(N-Benzyl-butylamino)-2-chloro-4-(1-oxido-thiomorpholino)-pyrimido-[5,4-d]-pyrimidine M.p.: 153°–155° C.;

8-Anilino-2-chloro-4-morpholino-pyrimido-[5,4-d]-pyrimidine M.p.: 193°–195° C.;

8-Anilino-2-chloro-4-(1-oxido-thiomorpholino)-pyrimido-[5,4-d]-pyrimidine M.p.: 230°–232° C.;

2-Chloro-8-(N-methylanilino)-4-morpholino-pyrimido-[5,4-d]-pyrimidine M.p.: 150°–152° C.;

2-Chloro-8-(N-methylanilino)-4-(1-oxido-thiomorpholino)-pyrimido-[5,4-d]-pyrimidine M.p.: 237°–239° C.;

2-Chloro-8-(2-hydroxyethylamino)-4-(1-oxido-thiomorpholino)-pyrimido-[5,4-d]-pyrimidine M.p.: 227°–229° C.;

2-Chloro-8-(4-hydroxybutylamino)-4-(1-oxido-thiomorpholino)-pyrimido-[5,4-d]-pyrimidine M.p.: 179°–181° C.;

2-Chloro-8-diethanolamino-4-thiomorpholino-pyrimido-[5,4-d]-pyrimidine M.p.: 121°–123° C.;

2-Chloro-8-diethanolamine-4-(1-oxido-thiomorpholino)-pyrimido-[5,4-d]-pyrimidine M.p.: 187°–189° C.;

2-Chloro-8-diisopropanolamino-4-(1-oxido-thiomorpholino)-pyrimido-[5,4-d]-pyrimidine M.p.: 205°–208° C.;

2-Chloro-8-[N-(2-hydroxyethyl)-2-methoxyethylamino]-4-(1-oxido-thiomorpholino)-pyrimido-[5,4-d]-pyrimidine M.p.: 143°–145° C.;

8-[N-Benzyl-(2-hydroxyethylamino)]-2-chloro-4-(1-oxido-thiomorpholino)-pyrimido-[5,4-d]-pyrimidine M.p.: 153°–155° C.;

2-Chloro-4-(1-oxido-thiomorpholino)-8-(3-picolylamino)-pyrimido-[5,4-d]-pyrimidine M.p.: 227°–229° C.;

2-Chloro-8-[N-methyl-(3-picolylamino)]-4-(1-oxido-thiomorpholino)-pyrimido-[5,4-d]-pyrimidine M.p.: 154°–156° C.;

2-Chloro-8-furfurylamino-4-(1-oxido-thiomorpholino)-pyrimido-[5,4-d]-pyrimidine M.p.: 203°–205° C.;

2-Chloro-8-(4-fluorobenzylamino)-4-(1-oxido-thiomorpholino)-pyrimido-[5,4-d]-pyrimidine M.p.: 210°–212° C.;

2-Chloro-8-(4-chlorobenzylamino)-4-(1-oxido-thiomorpholino)-pyrimido-[5,4-d]-pyrimidine M.p.: 216°–218° C.;

2-Chloro-8-(3-chlorobenzylamino)-4-(1-oxido-thiomorpholino)-pyrimido-[5,4-d]-pyrimidine M.p.: 239°–241° C.;

2-Chloro-8-(2-chlorobenzylamino)-4-(1-oxido-thiomorpholino)-pyrimido-[5,4-d]-pyrimidine M.p.: 238°–240° C.;

2-Chloro-8-(4-methylbenzylamino)-4-(1-oxido-thiomorpholino)-pyrimido-[5,4-d]-pyrimidine M.p.: 185°–187° C.;

2-Chloro-8-(3,4-dichlorobenzylamino)-4-(1-oxido-thiomorpholino)-pyrimido-[5,4-d]-pyrimidine M.p.: 259°–261° C.;

2-Chloro-8-(2,4-dichlorobenzylamino)-4-(1-oxido-thiomorpholino)-pyrimido-[5,4-d]-pyrimidine M.p.: 196°–198° C.;

2-Chloro-8-(3,4-dimethoxybenzylamino)-4-(1-oxido-thiomorpholino)-pyrimido-[5,4-d]-pyrimidine M.p.: 218°–220° C.;

2-Chloro-8-(3,4-methylenedioxy-benzylamino)-4-(1-oxide-thiomorpholino)-pyrimido-[5,4-d]-pyrimidine M.p.: 239°–241° C.;

2-Chloro-8-(3,4-dimethoxyphenethylamino)-4-(1-oxido-thiomorpholino)-pyrimido-[5,4-d]-pyrimidine M.p.: 214°–216° C.;

2-Chloro-8-[N-(3,4-dimethoxyphenethyl)-methylamino]-4-(1-oxido-thiomorpholino)-pyrimido-[5,4-d]-pyrimidine M.p.: 178°–179° C.;

8-(4-Ethoxyanilino)-2-chloro-4-(1-oxido-thiomorpholino)-pyrimido-[5,4-d]-pyrimidine M.p.: 237°–240° C.;

2-Chloro-4-(1-oxide-thiomorpholino)-8-(3-trifluoromethylanilino)-pyrimido-[5,4-d]-pyrimidine M.p.: 215°–218° C.

PREPARATION OF END PRODUCTS OF THE FORMULA I

Example 1

8-Benzylthio-4-morpholino-2-piperazino-pyrimido-[5,4-d]-pyrimidine

A solution of 103 gm (1.2 mol) of anhydrous piperazine in 1.5 liters of acetone was added, while stirring, to a suspension of 112 gm (0.3 mol) of 8-benzylthio-2-chloro-4-morpholino-pyrimido-[5,4-d]-pyrimidine in 1.5 liters of acetone, and the resulting mixture was heated, while stirring, to 50° C. and kept at this temperature for about 20 minutes. After cooling, the precipitate which had formed was suction-filtered off and digested with about 1 liter of water. After suction-filtering once more, the filter cake was washed with about 200 ml of methanol and dried at 60° C.

Yield: 108 gm (85% of theory),

M.p.: 179°–181° C.

For purification, the crude product was dissolved in 1.25 liters of chloroform or about 2 liters of methylene chloride at room temperature, and a small amount of an insoluble by-product was removed by filtration. The filtrate was admixed with 260 ml of 1N hydrochloric acid while stirring, whereby the hydrochloride of 8-benzylthio-4-morpholino-2-piperazino-pyrimido-[5,4-d]-pyrimidine was obtained as a fine crystalline precipitate. After standing for a short time, the hydrochloride was suction-filtered off and washed with a little ethanol. To liberate the base, the hydrochloride was suspended in about 3 liters of an ethanol-water mixture (1:1) and admixed, while stirring with 500 ml of 2N ammonia. After stirring for several hours, the precipitate which had formed was suction-filtered off, washed first with water and then with ethanol, and dried at about 100° C.

Yield: 97 gm (76% of theory),

M.p.: 191°–193° C.

$C_{21}H_{25}N_7OS$ (423.6) Calc.: C—59.55%; H—5.95%; N—23.15%; S—7.57% Found: C—59.72%; H—6.13%; N—23.10%; S—7.58%.

The same compound was obtained in analogous manner by heating for 30 minutes 8-benzylthio-4-morpholino-2-phenoxy-pyrimido-[5,4-d]-pyrimidine (m.p.: 159°–161° C.; prepared from 8-benzylthio-2-chloro-4-morpholino-pyrimido-[5,4-d]-pyrimidine and sodium phenolate) with piperazine at 90°–100° C., or by heating for 3 hours 4,8-bis(benzylthio)-2-piperazino-pyrimido-[5,4-d]-pyrimidine (m.p.: 213°–215° C., prepared from 4,8-bis(benzylthio)-2-chloro-pyrimido-[5,4-d]-(pyrimidine and piperazine in acetone) with morpholine and morpholine hydrochloride at about 60° C. The following salts were prepared by reacting 8-benzylthio-4-morpholino-2-piperazino-pyrimido-[5,4-d]-pyrimidine with an excess of the corresponding acid in aqueous solution:

M.p. of the hydrochloride: >270° C. (decomp.)

M.p. of the acetate: 181°–183° C.

M.p. of the maleate: 203°–205° C. (decomp.)

M.p. of the succinate: approx. 200° C.

M.p. of the salicylate: 225° C. (decomp.)

M.p. of the methanesulfonate: 285° C. (decomp.)

M.p. of the tosylate: 220°–230° C.

Example 2

8-Ethylthio-4-(1-oxido-thiomorpholino)-2-piperazino-pyrimido-[5,4-d]-pyrimidine

A solution of 3,4 gm (0.01 mol) of 8-ethylthio-2-chloro-4-(1-oxido-thiomorpholino)-pyrimido-[5,4-d]-pyrimidine (m.p. 197°–199° C.) in 100 ml of dimethylsulfoxide was slowly poured, while stirring, into a solution of 4.3 gm (0.05 mol) of piperazine in 75 ml of dimethylsulfoxide at 40° C., and the mixture was stirred for 1 hour at 40° C. The reaction mixture was then taken up in about 1 liter of water, whereby the reaction product slowly precipitated in crystalline form. After standing for a short period of time, the precipitate was suction-filtered off, washed with water and dried at about 70° C.

Yield: 3.6 gm (90% of theory),

M.p.: 202°–204° C.

After reprecipitation from 0.1N hydrochloric acid with 2N ammonia, the 8-ethylthio-4-(1-oxido-thiomorpholino)-2-piperazino-pyrimido-[5,4-d]-pyrimidine melted at 205°–206° C.

$C_{16}H_{23}N_7OS_2 \times 0.5\ H_2O$ (402.6) Calc.: C—47.74%; H—6.01%; N—24.36%; S—15.93% Found: C—47.85%; H—6.07%; N—24.40%; S—15.95%.

Example 3

2-(N-Formyl-piperazino)-8-methylthio-4-morpholino-pyrimido-[5,4-d]-pyrimidine 10.4 gm (0.035 mol) of 2-chloro-8-methylthio-4-morpholino-pyrimido-[5,4-d]-pyrimidine (m.p. 179°–180° C.) were heated with 28.5 gm (0.25 mol) of N-formyl-piperazine at about 100° C. for 30 minutes. The resulting solution was taken up in about 300 ml of water, whereby the reaction product was obtained as yellowish precipitate. The precipitate was suction-filtered off, washed with water and dried at 70° C.

Yield: 12.1 gm (92% of theory).

After recrystallization from ethanol/dioxane (2:1), the 2-(N-formyl-piperazino)-8-methylthio-4-morpholino-pyrimido-[5,4-d]-pyrimdine melted at 205°–207° C.

$C_{16}H_{21}N_7O_2S$ (375.5) Calc.: C—51.19%; H—5.64%; N—26.12%; S—8.54% Found: C—51.20%; H—5.65%; N—26.00%; S—8.39%.

Example 4

8-Methylthio-4-morpholino-2-piperazino-pyrimido-[5,4-d]-pyrimidine 1.5 gm (0.004 mol) of 2-(N-formyl-piperazino)-8-methylthio-4-morpholino-pyrimido-[5,4-d]-pyrimidine (m.p.: 205°–207° C.) were dissolved in 200 ml of absolute ethanol. After addition of 10 ml of ethanolic hydrochloric acid, the solution was refluxed for 20 minutes. The solvent was then evaporated in vacuo, and the residue was taken up in about 50 ml of water. The resulting solution of the hydrochloride was adjusted to about pH 10, whereby the free base was obtained as an initially oily precipitate which soon solidified. The precipitate was suction-filtered off, washed well with water and dried.

Yield: 1.2 gm (86% of theory).

After reprecipitation from 0.1N hydrochloric acid with ammonia, the 8-methylthio-4-morpholino-2-piperazino-pyrimido-[5,4-d]-pyrimidine melted at 163°–166° C.

$C_{15}H_{21}N_7OS$ (347.5) Calc.: C—51.85%; H—6.09%; N—28.22%; S—9.23% Found: C—51.65%; H—6.10%; N—28.00%; S—9.26%.

Example 5

2-(N-Acetoacetyl-piperazino)-8-methylthio-4-thiomorpholinopyrimido-[5,4-d]-pyrimidine 1.6 gm (0.02 mol) of diketene were slowly poured, while stirring, into a solution of 3.6 gm (0.01 mol) of 8-methylthio-2-piperazino-4-thiomorpholino-pyrimido-[5,4-d]-pyrimidine (m.p.: 177°–179° C.) in 50 ml of dioxane. After stirring for 30 minutes more, the solvent was evaporated in vacuo, and the residue was taken up in about 100 ml of water. The precipitated reaction product was suction-filtered off, washed with water and dried.

Yield: 3.3 gm (74% of theory).

After recrystallization from ethanol the 2-(N-acetoacetyl-piperazino)-8-methylthio-4-thiomorpholino-pyrimido-[5,4-d]-pyrimidine melted at 174°–176° C.

$C_{19}H_{25}N_7O_2S_2$ (447.6) Calc.: C—50.99%; H—5.63%; N—21.91%; S—14.33% Found: C—51.10%; H—5.69%; N—21.85%; S—14.25%.

Example 6

2-(N-Acetyl-piperazino)-8-benzylthio-4-morpholino-pyrimido-[5,4-d]-pyrimidine

A suspension of 2.1 gm (0.005 mol) of 8-benzylthio-4-morpholino-2-piperazino-pyrimido-[5,4-d]-pyrimidine (m.p.: 191°–193° C.) in 150 ml of acetone was refluxed for 30 minutes after addition of 0.8 gm (0.01 mol) of acetyl chloride. The solvent was then evaporated in vacuo, and the residue was taken up in approximately 200 ml of water. The reaction product was suction-filtered off, washed with water and dried.

After recrystallization from dioxane the 2-(N-acetyl-piperazino)-8-benzylthio-4-morpholino-pyrimido-[5,4-d]-pyrimidine melted at 237°–239° C.

$C_{23}H_{27}N_7O_2S$ (465.6) Calc.: C—59.33%; H—5.85%; N—21.06%; S—6.89% Found: C—59.00%; H—5.86%; N—20.92%; S—6.84%.

Example 7

8-Methylthio-2-piperazino-4-thiomorpholino-pyrimido-[5,4-d]-pyrimidine

This compound was prepared analogous to Example 2 from 2-chloro-8-methylthio-4-thiomorpholino-pyrimido-[5,4-d]-pyrimidine (m.p.: 165°–167° C.) and piperazine at room temperature.

M.p. 177°–179° C.

The substance was obtained analogous to Example 4 from 2-(N-formyl-piperazine)-8-methylthio-4-thiomorpholino-pyrimido-[5,4-d]-pyrimidine (m.p.: 199°–202° C.).

Example 8

8-Methylthio-4-(1-oxido-thiomorpholino)-2-piperazino-pyrimido-[5,4-d]-pyrimidine This compound was prepared analogous to Example 2 from 2-chloro-8-methylthio-4-(1-oxido-thiomorpholino)-pyrimido-[5,4-d]-pyrimidine (m.p. 252°–254° C.) and piperazine at 50° C.

M.p.: 253°–255° C.

The substance was also obtained from 8-methylthio-2-piperazino-4-thiomorpholino-pyrimido[5,4-d]-pyrimidine (m.p.: 177°–179° C.) by oxidation with sodium metaperiodate under reflux in methanol.

Example 9

4-Morpholino-2-piperazino-8-propylthio-pyrimido-[5,4-d]-pyrimidine

This compound was prepared analogous to Example 1 from 2-chloro-4-morpholino-8-propylthio-pyrimido-[5,4-d]-pyrimidine (m.p.: 126°–128° C.) and piperazine.

M.p.: 146°–149° C. (ethyl acetate).

Example 10

8-Isopropylthio-4-morpholino-2-piperazino-pyrimido-[5,4-d]-pyrimidine

This compound was prepared analogous to Example 1 from 2-chloro-8-isopropylthio-4-morpholino-pyrimido-[5,4-d]-pyrimidine (m.p.: 132°–134° C.) and piperazine.

M.p.: 179°–182° C.

Example 11

8-Butylthio-4-morpholino-2-piperazino-pyrimido-[5,4-d]-pyrimidine

This compound was prepared analogous to Example 1 from 8-butylthio-2-chloro-4-morpholino-pyrimido-[5,4-d]-pyrimidine (m.p.: 132°–133° C.) and piperazine.
M.p.: 148°–151° C. (ethyl acetate).

Example 12

4-Morpholino-8-pentylthio-2-piperazino-pyrimido-[5,4-d]-pyrimidine

This compound was prepared analogous to Example 1 from 2-chloro-4-morpholino-8-pentylthio-pyrimido-[5,4-d]-pyrimidine (m.p.: 84°–87° C.) and piperazine.
M.p.: 114°–117° C. (methanol).

Example 13

4-Morpholino-8-octylthio-2-piperazino-pyrimido-[5,4-d]-pyrimidine

This compound was prepared analogous to Example 1 from 2-chloro-4-morpholino-8-octylthio-pyrimido-[5,4-d]-pyrimidine (m.p.: 66°–69° C.) and piperazine.
M.p.: 118°–121° C. (ethyl acetate).

Example 14

8-Cyclohexylthio-4-morpholino-2-piperazino-pyrimido-[5,4-d]-pyrimidine

This compound was prepared analogous to Example 1 from 2-chloro-8-cyclohexylthio-4-morpholino-pyrimido-[5,4-d]-pyrimidine (m.p.: 179°–181° C.) and piperazine.
M.p.: 193°–196° C.

Example 15

4-Morpholino-8-phenylthio-2-piperazino-pyrimido-[5,4-d]-pyrimidine

This compound was prepared analogous to Example 2 from 2-chloro-4-morpholino-8-phenylthio-pyrimido-[5,4-d]-pyrimidine (m.p.: 196°–197° C.) and piperazine.
M.p.: 177°–180° C. (methanol).

Example 16

8-Phenylthio-2-piperazino-4-thiomorpholino-pyrimido-[5,4-d]-pyrimidine

This compound was prepared analogous to Example 2 from 2-chloro-8-phenylthio-4-thiomorpholino-pyrimido-[5,4-d]-pyrimidine (m.p.: 236°–238° C.) and piperazine.
M.p.: 190°–192° C.

Example 17

4-(1-Oxido-thiomorpholino)-8-phenylthio-2-piperazino-pyrimido-[5,4-d]-pyrimidine This compound was prepared analogous to Example 2 from 2-chloro-4-(1-oxido-thiomorpholino)-8-phenylthio-pyrimido-[5,4-d]-pyrimidine (m.p.: 253°–255° C.) and piperazine.
M.p.: 203°–205° C.

Example 18

8-Benzylthio-2-piperazino-4-thiomorpholino-pyrimido-[5,4-d]-pyrimidine

This compound was prepared analogous to Example 1 from 8-benzylthio-2-chloro-4-thiomorpholino-pyrimido-[5,4-d]-pyrimidine (m.p.: 162°–164° C.) and piperazine.
M.p.: 185°–187° C.

Example 19

8-Benzylthio-4-(1-oxido-thiomorpholino)-2-piperazino-pyrimido-[5,4-d]-pyrimidine This compound was prepared analogous to Example 2 from 8-benzylthio-2-chloro-4-(1-oxido-thiomorpholino)-pyrimido-[5,4-d]-pyrimidine (m.p.: 188°–190° C.) and piperazine.
M.p.: 206°–208° C.

Example 20

8-Benzylthio-4-(1,1-dioxido-thiomorpholino)-2-piperazino-pyrimido-[5,4-d]-pyrimidine This compound was prepared analogous to Example 1 from 8-benzylthio-2-chloro-4-(1,1-dioxido-thiomorpholino)-pyrimido-[5,4-d]-pyrimidine (m.p.: 238°–239° C.) and piperazine.
M.p.: 209°–211° C.

Example 21

8-Benzythio-2-homopiperazine-4-morpholino-pyrimido-[5,4-d]-pyrimidine

This compound was prepared analogous to Example 1 from 8-benzythio-2-chloro-4-morpholino-pyrimido-[5,4-d]-pyrimidine (m.p.: 159°–161° C.) and homopiperazine.
M.p.: 178°–180° C.

Example 22

4-Morpholino-8-phenethylthio-2-piperazino-pyrimido-[5,4-d]-pyrimidine

This compound was prepared analogous to Example 2 from 2-chloro-4-morpholino-8-phenethylthio-pyrimido-[5,4-d]-pyrimidine (m.p.: 148°–150° C.) and piperazine.
M.p.: 153°–155° C. (methanol):

Example 23

8-Phenethylthio-2-piperazino-4-thiomorpholino-pyrimido-[5,4-d]-pyrimidine

This compound was prepared analogous to Example 2 from 2-chloro-8-phenethylthio-4-thiomorpholino-pyrimido-[5,4-d]-pyrimidine (m.p.: 155°–157° C.) and piperazine.
M.p.: 125°–127° C. (methanol).

Example 24

4-(1-Oxido-thiomorpholino)-8-phenethylthio-2-piperazino-pyrimido-[5,4-d]-pyrimidine This compound was prepared analogous to Example 1 from 2-chloro-4-(1-oxido-thiomorpholino)-8-phenethylthio-pyrimido-[5,4-d]-pyrimidine (m.p.: 232°–234° C.) and piperazine.
M.p.: 188°–190° C.

Example 25

4-Morpholino-8-(3-phenylpropyl-thio)-2-piperazino-pyrimido-[5,4-d]-pyrimidine

This compound was prepared analogous to Example 1 from 2-chloro-4-morpholino-8-(3-phenylpropyl-thio)-pyrimido-[5,4-d]-pyrimidine (m.p.: 127°–129° C.) and piperazine.

M.p.: 110°–112° C.

Example 26

8-Benzylthio-4-(2-methylmorpholino)-2-piperazino-pyrimido-[5,4-d]-pyrimidine

This compound was prepared analogous to Example 1 from 8-benzylthio-2-chloro-4-(2-methylmorpholino)-pyrimido-[5,4-d]-pyrimidine (m.p.: 40°–60° C.) and piperazine.

M.p.: 175°–177° C.

Example 27

8-Benzylthio-4-(2,6-dimethyl-morpholino)-2-piperazino-pyrimido-[5,4-d]-pyrimidine This compound was prepared analogous to Example 1 from 8-benzylthio-2-chloro-(2,6-dimethyl-morpholino)-pyrimido-[5,4-d]-pyrimidine (m.p.: 85°–90° C.) and piperazine.

M.p.: 213°–215° C.

Example 28

8-(Methoxycarbonyl-methylthio)-4-morpholino-2-piperazino-pyrimido-[5,4-d]-pyrimidine This compound was prepared analogous to Example 2 from 2-chloro-8-(methoxycarbonyl-methylthio)-4-morpholino-pyrimido-[5,4-d]-pyrimidine (m.p.: 188°–190° C.) and piperazine.

M.p.: 205°–207° C. (ethanol).

Example 29

8-(2-Diethylamino-ethylthio)-4-morpholino-2-piperazino-pyrimido-[5,4-d]-pyrimidine This compound was prepared analogous to Example 2 from 2-chloro-8-(2-diethylamino-ethylthio)-4-morpholino-pyrimido-[5,4-d]-pyrimidine (resin) and piperazine.

M.p.: 109°–111° C.

Example 30

8-(2-Diethylamino-ethylthio)-4-(1-oxido-thiomorpholino)-2-piperazino-pyrimido-[5,4-d]-pyrimidine This compound was prepared analogous to Example 2 from 2-chloro-8-(2-diethylamino-ethylthio)-4-(1-oxido-thiomorpholino)-pyrimido-[5,4-d]-pyrimidine (m.p.: 95°–99° C.) and piperazine.

M.p.: 136°–138° C. (methanol).

Example 31

8-(2-Hydroxyethylthio)-4-(1-oxido-thiomorpholino)-2-piperazino-pyrimido-[5,4-d]-pyrimidine This compound was prepared analogous to Example 1 from 2-chloro-8-(2-hydroxy-ethylthio)-4-(1-oxido-thiomorpholino)-pyrimido-[5,4-d]-pyrimidine (m.p.: 228°–230° C., decomposition) and piperazine.

M.p.: 200°–202° C. (ethanol).

Example 32

8-(4-Methoxybenzylthio)-4-morpholino-2-piperazino-pyrimido-[5,4-d]-pyrimidine

This compound was prepared analogous to Example 1 from 2-chloro-8-(4-methoxy-benzylthio)-4-morpholino-pyrimido-[5,4-d]-pyrimidine (m.p.: 173°–174° C.) and piperazine.

M.p.: 181°–183° C. (ethanol).

Example 33

8-3,4-Dimethoxybenzylthio)-4-morpholino-2-piperazino-pyrimido-[5,4-d]-pyrimidine This compound was prepared analogous to Example 1 from 2-chloro-8-(3,4-dimethoxy-benzylthio)-4-morpholino-pyrimido-[5,4-d]-pyrimidine (m.p.: 143°–145° C.) and piperazine.

M.p.: 141°–143° C. (methanol).

Example 34

8-(4-Methylbenzylthio)-4-morpholino-2-piperazino-pyrimido-[5,4-d]-pyrimidine

This compound was prepared analogous to Example 1 from 2-chloro-8-(4-methylbenzyl-thio)-4-morpholino-pyrimido-[5,4-d]-pyrimidine (m.p.: 177°–179° C.) and piperazine.

M.p.: 189°–191° C.

Example 35

8-(4-Fluorobenzylthio)-4-morpholino-2-piperazino-pyrimido-[5,4-d]-pyrimidine

This compound was prepared analogous to Example 1 from 2-chloro-8-(fluorobenzyl-thio)-4-morpholino-pyrimido-[5,4-d]-pyrimidine (m.p.: 163°–165° C.) and piperazine.

M.p.: 192°–194° C.

Example 36

8-(4-Chlorobenzyl-thio)-4-morpholino-2-piperazino-pyrimido-[5,4-d]-pyrimidine

This compound was prepared analogous to Example 1 from 2-chloro-8-(4-chlorobenzyl-thio)-4-morpholino-pyrimido-[5,4-d]-pyrimidine (m.p.: 135°–145° C.) and piperazine.

M.p.: 207°–209° C.

Example 37

8-(2,4-Dichlorobenzylthio)-4-morpholino-2-piperazino-pyrimido-[5,4-d]-pyrimidine This compound was prepared analogous to Example 1 from 2-chloro-8-(2,4-dichlorobenzylthio)-4-morpholino-pyrimido-[5,4-d]-pyrimidine (m.p.: 175°–177° C.) and piperazine.

M.p.: 188°–190° C. (ethanol).

Example 38

8-(4-Hydroxyphenylthio)-4-morpholino-2-piperazino-pyrimido-[5,4-d]-pyrimidine

This compound was prepared analogous to Example 2 from 2-chloro-8-(4-hydroxy-phenylthio)-4-morpholino-pyrimido-[5,4-d]-pyrimidine (m.p.: >300° C.) and piperazine.

M.p.: 246°–248° C. (ethanol).

Example 39

8-(4-Hydroxyphenyl-thio)-2-(N-hydroxyethyl-piperazino)-4-morpholino-pyrimido-[5,4-d]-pyrimidine This compound was prepared analogous to Example 2 from 2-chloro-8-(4-hydroxy-phenyl-thio)-4-morpholino-pyrimido-[5,4-d]-pyrimidine (m.p.: >300° C.) and N-hydroxyethyl-piperazine.
M.p.: 214°–215° C. (methanol).

Example 40

2-(N-Hydroxyethyl-piperazino)-8-methylthio-4-morpholino-pyrimido-[5,4-d]-pyrimidine This compound was prepared analogous to Example 2 from 2-chloro-8-methylthio-4-morpholino-pyrimido-[5,4-d]-pyrimidine (m.p.: 179°–180° C.) and N-hydroxyethyl-piperazine.
M.p.: 167°–168° C. (methanol).

Example 41

8-Ethylthio-2-(N-hydroxyethyl piperazino)-4-(1-oxido-thiomorpholino)-pyrimido-[5,4-d]-pyrimidine This compound was prepared analogous to Example 2 from 8-ethylthio-2-chloro-4-(1-oxido-thiomorpholino)-pyrimido-[5,4-d]-pyrimidine (m.p.: 197°–199° C.) and N-hydroxyethyl-piperazine.
M.p.: 197°–198° C. (methanol).

Example 42

2-(N-Hydroxyethyl-piperazino)-4-morpholino-8-phenylthio-pyrimido-[5,4-d]-pyrimidine This compound was prepared analogous to Example 2 from 2-chloro-4-morpholino-8-phenylthio-pyrimido-[5,4-d]-pyrimidine (m.p. : 196°–197° C.) and N-hydroxyethyl piperazine.
M.p.: 156°–158° C. (methanol).

Example 43

8-Benzylthio-2-(N-hydroxyethyl-piperazino)-4-morpholino-pyrimido-[5,4-d]-pyrimidine This compound was prepared analogous to Example 2 from 8-benzylthio-2-chloro-4-morpholino-pyrimido-[5,4-d]-pyrimidine (m.p.: 159°–161° C.) and N-hydroxyethyl-piperazine.
M.p.: 165°–167° C. (ethyl acetate).

Example 44

8-Benzylthio-2-(N-hydroxyethyl piperazino)-4-(1-oxido-thiomorpholino)-pyrimido-[5,4-d]-pyrimidine This compound was prepared analogous to Example 2 from 8-benzylthio-2-chloro-4-(1-oxido-thiomorpholino)-pyrimido-[5,4-d]-pyrimidine (m.p.: 188°–190° C.) and N-hydroxyethyl-piperazine.
M.p.: 211°–213° C. (ethanol).

Example 45

2-(N-Hydroxyethyl-piperazino)-4-(1-oxido-thiomorpholino)-8-phenethylthio-pyrimido-[5,4-d]-pyrimidine This compound was prepared analogous to Example 2 from 2-chloro-4-(1-oxido-thiomorpholino)-8-phenethylthio-pyrimido-[5,4-d]-pyrimidine (m.p.: 232°–234° C.) and N-hydroxyethyl-piperazine.
M.p.: 168°–170° C. (methanol).

Example 46

8-Benzylthio-2-(N-methyl-piperazino)-4-(1-oxido-thiomorpholino)-pyrimido-[5,4-d]-pyrimidine This compound was prepared analogous to Example 1 from 8-benzylthio-2-chloro-4-(1-oxido-thiomorpholino)-pyrimido-[5,4-d]-pyrimidine (m.p.: 188°–190° C.) and N-methyl-piperazine.
M.p.: 198°–200° C. (dioxane).

Example 47

2-(N-Ethyl-piperazino)-8-benzylthio-4-morpholino-pyrimido-[5,4-d]-pyrimidine This compound was prepared analogous to Example 1 from 8-benzylthio-2-chloro-4-morpholino-pyrimido-[5,4-d]-pyrimidine (m.p.: 159°–161° C.) and N-ethyl-piperazine.
M.p.: 161°–163° C. (ethanol).

Example 48

8-Benzylthio-2-[N-(2-hydroxy-propyl)-piperazino]-4-morpholino-pyrimido-[5,4-d]-pyrimidine This compound was prepared analogous to Example 1 from 8-benzylthio-2-chloro-4-morpholino-pyrimido-[5,4-d]-pyrimidine (m.p.: 159°–161° C.) and N-(2-hydroxy-propyl)-piperazine.
M.p.: 173°–176° C. (ethanol).

Example 49

8-Benzylthio-2-(N-isobutyl-piperazino)-4-morpholino-pyrimido-[5,4-d]-pyrimidine This compound was prepared analogous to Example 1 from 8-benzylthio-2-chloro-4-morpholino-pyrimido-[5,4-d]-pyrimidine (m.p.: 159°–161° C.) and N-isobutyl-piperazine.
M.p.: 152°–155° C. (ethyl acetate).

Example 50

8-Benzylthio-4-morpholino-2-(N-pentyl-piperazino)-pyrimido-[5,4-d]-pyrimidine This compound was prepared analogous to Example 1 from 8-benzylthio-2-chloro-4-morpholino-pyrimido-[5,4-d]-pyrimidine (m.p: 159°–161° C.) and N-pentyl-piperazine.
M.p.: 143°–146° C. (ethanol).

Example 51

8-Benzylthio-4-morpholino-2-(N-phenyl-piperazino)-pyrimido-[5,4-d]-pyrimidine This compound was prepared analogous to Example 1 from 8-benzylthio-2-chloro-4-morpholino-pyrimido-[5,4-d]-pyrimidine (m.p.: 159°–161° C.) and n-phenyl-piperazine.
M.p.: 226°–228° C. (dioxane).

Example 52

2-(N-Benzyl-piperazino)-8-benzylthio-4-morpholino-pyrimido-[5,4-d]-pyrimidine This compound was prepared analogous to Example 1 from 8-benzylthio-2-chloro-4-morpholino-pyrimido-[5,4-d]-pyrimidine (m.p.: 159°–161° C.) and N-benzyl-piperazine.
M.p.: 138°–141° C. (ethanol).

Example 53

8-Methoxy-4-morpholino-2-piperazino-pyrimido-[5,4-d]-pyrimidine

This compound was prepared analogous to Example 2 from 2-chloro-8-methoxy-4-morpholino-pyrimido-[5,4-d]-pyrimidine (m.p.: 160°–162° C.) and piperazine.
M.p.: 165°–167° C. (methanol).

Example 54

8-Methoxy-4-(1-oxido-thiomorpholino)-2-piperazino-pyrimido-[5,4-d]-pyrimidine

This compound was prepared analogous to Example 2 from 2-chloro-8-methoxy-4-(1-oxido-thiomorpholino)-pyrimido-[5,4-d]-pyrimidine (m.p.: 218°–221° C.) and piperazine.
M.p.: 219°–221° C.

Example 55

8-Ethoxy-4-morpholino-2-piperazino-pyrimido-[5,4-d]-pyrimidine

This compound was prepared analogous to Example 2 from 8-ethoxy-2-chloro-4-morpholino-pyrimido-[5,4-d]-pyrimidine (m.p.: 153°–155° C.) and piperazine.
M.p.: 168°–170° C.

Example 56

8-(2-Hydroxyethoxy)-4-morpholino-2-piperazino-pyrimido-[5,4-d]-pyrimidine

This compound was prepared analogous to Example 1 from 2-chloro-8-(2-hydroxy-ethoxy)-4-morpholino-pyrimido-[5,4-d]-pyrimidine (m.p: 190°–195° C.) and piperazine.
M.p.: 182°–184° C. (methanol).

Example 57

8-Ethylthio-2-(N-formyl-piperazino)-4-thiomorpholino-pyrimido-[5,4-d]-pyrimidine This compound was prepared analogous to Example 3 from 8-ethylthio-2-chloro-4-thiomorpholino-pyrimido-[5,4-d]-pyrimidine (m.p.: 134°–136° C.) and N-formyl-piperazine.
M.p.: 165°–167° C. (ethanol).

Example 58

8-Benzylthio-2-(N-formyl-piperazino)-4-morpholino-pyrimido-[5,4-d]-pyrimidine

This compound was prepared analogous to Example 2 from 8-benzylthio-2-chloro-4-morpholino-pyrimido-[5,4-d]-pyrimidine (m.p.: 159°–161° C.) and N-formyl-piperazine.
M.p.: 228°–230° C. (ethyl acetate).

This substance was also obtained from 8-benzylthio-4-morpholino-2-piperazino-pyrimido-[5,4-d]-pyrimidine (m.p.: 191°–193° C.) by refluxing with chloral hydrate in chloroform.

Example 59

8-Benzylthio-2-(N-methoxyacetyl-piperazino)-4-morpholino-pyrimido-[5,4-d]-pyrimidine This compound was prepared analogous to Example 6 from 8-benzylthio-4-morpholino-2-piperzino-pyrimido-[5,4-d]-pyrimidine (m.p.: 191°–193° C.) and methoxyacetyl chloride.
M.p.: 174°–176° C. (ethanol).

Example 60

2-(N-Acetoacetyl-piperazino)-8-benzylthio-4-morpholino-pyrimido-[5,4-d]-pyrimidine This compound was prepared analogous to Example 6 from 8-benzylthio-4-morpholino-2-piperazino-pyrimido-[5,4-d]-pyrimidine (m.p.: 191°–193° C.) and diketene.
M.p.: 189°–191° C. (ethanol).

Example 61

8-Benzylthio-2-(N-formyl-piperazino)-4-(1-oxido-thiomorpholino)-pyrimido-[5,4-d]-pyrimidine This compound was prepared analogous to Example 1 from 8-benzylthio-2-chloro-4-(1-oxido-thiomorpholino)-pyrimido-[5,4-d]-pyrimidine (m.p.: 188°–190° C.) and N-formyl-piperazine.
M.p.: 246°–248° C. (methanol).

Example 62

2-(N-Formyl-piperazino)-4-morpholino-8-phenethylthio-pyrimido-[5,4-d]-pyrimidine This compound was prepared analogous to Example 1 from 2-chloro-4-morpholino-8-phenethylthio-pyrimido-[5,4-d]-pyrimidine (m.p.: 148°–150° C.) and N-formyl-piperazine.
M.p.: 105°–107° C. (ethanol).

Example 63

8-Benzylthio-4-morpholino-2-(N-nicotinoyl-piperazino)-pyrimido-[5,4-d]-pyrimidine This compound was prepared analogous to Example 6 from 8-benzylthio-4-morpholino-2-piperazino-pyrimido-[5,4-d]-pyrimidine (m.p.: 191°–193° C.) and nicotinic acid chloride hydrochloride in dry pyridine.
M.p.: 203°–205° C. (dioxane).

Example 64

2-(N-Acetylsalicyloyl-piperazino)-8-benzylthio-4-morpholino-pyrimido-[5,4-d]-pyrimidine This compound was prepared analogous to Example 6 from 8-benzylthio-4-morpholino-2-piperazino-pyrimido-[5,4-d]-pyrimidine (m.p.: 191°–193° C.) and acetylsalicylic acid anhydride.
M.p.: 253°–255° C. (dioxane).

Example 65

8-Benzylthio-2-[N-(2-carboxyethyl-carbonyl)-piperazino]-4-morpholino-pyrimido-[5,4-d]-pyrimidine This compound was prepared analogous to Example 6 from 8-benzylthio-4-morpholino-2-piperazino-pyrimido-[5,4-d]-pyrimidine (m.p.: 191°–193° C.) and succinic acid anhydride.
M.p.: 236°–237° C. (dioxane).

Example 66

8-Benzylthio-2-[N-(3-carboxypropyl-carbonyl)-piperazino]-4-morpholino-pyrimido-[5,4-d]-pyrimidine This compound was prepared analogous to Example 6 from 8-benzylthio-4-morpholino-2-piperazino-pyrimido-[5,4-d]-pyrimidine (m.p.: 191°–193° C.) and glutaric acid anhydride.
M.p.: 216°–218° C. (dioxane).

Example 67

8-Benzylthio-2-[N-(2-furoyl)-piperazino]-4-morpholino-pyrimido-[5,4-d]-pyrimidine

This compound was prepared analogous to Example 6 from 8-benzylthio-4-morpholino-2-piperazino-pyrimido-[5,4-d]-pyrimidine (m.p.: 191°–193° C.) and furan-2-carboxylic acid chloride in dry pyridine.

M.p.: 235°–237° C. (ethanol/dioxane).

Example 68

4-Morpholino-2-piperazino-8-(4-tolylthio)-pyrimido-[5,4-d]-pyrimidine

This compound was prepared analogous to Example 1 from 2-chloro-4-morpholino-8-(4-tolylthio)-pyrimido-[5,4-d]-pyrimidine (m.p.: 163°–165° C.) and piperazine.

M.p.: 170°–174° C. (ethyl acetate).

Example 69

8-(4-Methoxyphenyl-thio)-4-morpholino-2-piperazino-pyrimido-[5,4-d]-pyrimidine

This compound was prepared analogous to Example 1 from 2-chloro-8-(4-methoxyphenyl-thio)-4-morpholino-pyrimido-[5,4-d]-pyrimidine (m.p.: 196°–199° C.) and piperazine.

M.p.: 174°–177° C.

Example 70

8-(2-Aminophenyl-thio)-4-morpholino-2-piperazino-pyrimido-[5,4-d]-pyrimidine

This compound was prepared analogous to Example 1 from 8-(2-aminophenyl-thio)-2-chloro-4-morpholino-pyrimido-[5,4-d]-pyrimidine (m.p.: 151°–153° C.) and piperazine.

M.p.: 174°–177° C. (ethyl acetate).

Example 71

8-(4-Chlorophenyl-thio)-4-morpholino-2-piperazino-pyrimido-[5,4-d]-pyrimidine

This compound was prepared analogous to Example 1 from 2-chloro-8-(4-chlorophenyl-thio)-4-morpholino-pyrimido-[5,4-d]-pyrimidine (m.p.: 208°–210° C.) and piperazine.

M.p.: 176°–178° C.

Example 72

8-(4-Fluorophenyl-thio)-4-morpholino-2-piperazino-pyrimido-[5,4-d]-pyrimidine

This compound was prepared analogous to Example 1 from 2-chloro-8-(4-fluorophenyl-thio)-4-morpholino-pyrimido-[5,4-d]-pyrimidine (m.p.: 213°–215° C.) and piperazine.

M.p.: 176°–178° C.

Example 73

8-(4-Bromophenyl-thio)-4-morpholino-2-piperazino-pyrimido-[5,4-d]-pyrimidine

This compound was prepared analogous to Example 1 from 8-(4-bromophenyl-thio)-2-chloro-4-morpholino-pyrimido-[5,4-d]-pyrimidine (m.p.: 205°–207° C.) and piperazine.

M.p.: 183°–185° C.

Example 74

8-(4-Bromophenyl-thio)-4-(1-oxido-thiomorpholino)-2-piperazino-pyrimido-[5,4-d]-pyrimidine

This compound was prepared analogous to Example 1 from 8-(4-bromophenyl-thio)-2-chloro-4-(1-oxido-thiomorpholino)-pyrimido-[5,4-d]-pyrimidine (m.p.: 272°–275° C.) and piperazine.

M.p.: 238°–240° C.

Example 75

8-(4-Chlorophenyl-thio)-4-(1-oxido-thiomorpholino)-2-piperazino-pyrimido-[5,4-d]-pyrimidine

This compound was prepared analogous to Example 1 from 2-chloro-8-(4-chlorophenyl-thio)-4-(1-oxido-thiomorpholino)-pyrimido-[5,4-d]-pyrimidine (m.p.: 267°–269° C.) and piperazine.

M.p.: 217°–219° C. (ethanol).

Example 76

8-(4-Hydroxyphenyl-thio)-4-(1-oxido-thiomorpholino)-2-piperazino-pyrimido-[5,4-d]-pyrimidine

This compound was prepared analogous to Example 1 from 2-chloro-8-(4-hydroxyphenyl-thio)-4-(1-oxido-thiomorpholino)-pyrimido-[5,4-d]-pyrimidine (m.p.: 280° C.) and piperazine.

M.p.: 262°–264° C. (ethanol).

Example 77

8-(4-Methoxyphenyl-thio)-4-(1-oxido-thiomorpholino)-2-piperazino-pyrimido-[5,4-d]-pyrimidine

This compound was prepared analogous to Example 1 from 2-chloro-8-(4-methoxyphenyl-thio)-4-(1-oxido-thiomorpholino)-pyrimido-[5,4-d]-pyrimidine (m.p.: 239°–241° C.) and piperazine.

M.p.: 224°–226° C. (ethanol).

Example 78

4-(1-Oxido-thiomorpholino)-2-piperazino-8-(4-tolyl-thio)-pyrimido-[5,4-d]-pyrimidine

This compound was prepared analogous to Example 1 from 2-chloro-4-(1-oxido-thiomorpholino)-8-(4-tolyl-thio)-pyrimido-[5,4-d]-pyrimidine (m.p.: 261°–263° C.) and piperazine.

M.p.: 247°–249° C. (ethanol).

Example 79

8-(2-Fluorobenzyl-thio)-4-morpholino-2-piperazino-pyrimido-[5,4-d]-pyrimidine

This compound was prepared analogous to Example 1 from 2-chloro-8-(2-fluorobenzyl-thio)-4-morpholino-pyrimido-[5,4-d]-pyrimidine (m.p.: 151°–153° C.) and piperazine.

M.p.: 170°–172° C.

Example 80

8-(3-Fluorobenzyl-thio)-4-morpholino-2-piperazino-pyrimido-[5,4-d]-pyrimidine

This compound was prepared analogous to Example 1 from 2-chloro-8-(3-fluorobenzyl-thio)-4-morpholino-pyrimido-[5,4-d]-pyrimidine (m.p.: 192°–194° C.) and piperazine.

M.p.: 176°–178° C.

Example 81

8-(2-Fluorobenzyl-thio)-4-(1-oxido-thiomorpholino)-2-piperazino-pyrimido-[5,4-d]-pyrimidine This compound was prepared analogous to Example 1 from 2-chloro-8-(2-fluorobenzyl-thio)-4-(1-oxido-thiomorpholino)-pyrimido-[5,4-d]-pyrimidine (m.p.: 206°–208° C.) and piperazine.

M.p.: 235°–237° C. (ethanol/water).

Example 82

8-(3-Fluorobenzyl-thio)-4-(1-oxido-thiomorpholino)-2-piperazino-pyrimido-[5,4-d]-pyrimidine This compound was prepared analogous to Example 1 from 2-chloro-8-(3-fluorobenzyl-thio)-4-(1-oxido-thiomorpholino)-pyrimido-[5,4-d]-pyrimidine (m.p.: 205°–207° C.) and piperazine.

M.p.: 225°–227° C.

Example 83

8-(2-Chlorobenzyl-thio)-4-morpholino-2-piperazino-pyrimido-[5,4-d]-pyrimidine

This compound was prepared analogous to Example 1 from 2-chloro-8-(2-chlorobenzyl-thio)-4-morpholino-pyrimido-[5,4-d]-pyrimidine (m.p.: 178°–180° C.) and piperazine.

M.p.: 180°–182° C.

Example 84

8-(2-Chlorobenzyl-thio)-4-(1-oxido-thiomorpholino)-2-piperazino-pyrimido-[5,4-d]-pyrimidine This compound was prepared analogous to Example 1 from 2-chloro-8-(2-chlorobenzyl-thio)-4-(1-oxido-thiomorpholino)-pyrimido-[5,4-d]-pyrimidine (m.p.: 203°–206° C.) and piperazine.

M.p.: 217°–219° C.

Example 85

8-(4-Chlorobenzyl-thio)-4-(1-oxido-thiomorpholino)-2-piperazino-pyrimido-[5,4-d]-pyrimidine This compound was prepared analogous to Example 1 from 2-chloro-8-(4-chlorobenzyl-thio)-4-(1-oxido-thiomorpholino)-pyrimido-[5,4-d]-pyrimidine (m.p.: 232°–234° C.) and piperazine.

M.p.: 231°–233° C.

Example 86

8-(3,4-Dichlorobenzyl-thio)-4-morpholino-2-piperazino-pyrimido-[5,4-d]-pyrimidine This compound was prepared analogous to Example 1 from 2-chloro-8-(3,4-dichlorobenzyl-thio)-4-morpholino-pyrimido-[5,4-d]-pyrimidine (m.p.: 153°–156° C.) and piperazine.

M.p.: 216°–218° C.

Example 87

8-(3,4-Dichlorobenzyl-thio)-4-(1-oxido-thiomorpholino)-2-piperazino-pyrimido-[5,4-d]-pyrimidine This compound was prepared analogous to Example 1 from 2-chloro-8-(3,4-dichlorobenzyl-thio)-4-)1-oxido-thiomorpholino)-pyrimido-[5,4-d]-pyrimidine (m.p.: 210°–212° C.) and piperazine.

M.p.: 230°–233° C.

Example 88

8-(2,4-Dichlorobenzyl-thio)-4-(1-oxido-thiomorpholino)-2-piperazino-pyrimido-[5,4-d]-pyrimidine This compound was prepared analogous to Example 1 from 2-chloro-8-(2,4-dichlorobenzyl-thio)-4-(1-oxido-thiomorpholino)-pyrimido-[5,4-d]-pyrimidine (m.p.: 227°–229° C.) and piperazine.

M.p.: 207°–209° C.

Example 89

4-Morpholino-2-piperazino-8-(3-trifluoromethylbenzyl-thio)-pyrimido-[5,4-d]-pyrimidine This compound was prepared analogous to Example 1 from 2-chloro-4-morpholino-8-(3-trifluoromethylbenzyl-thio)-pyrimido-[5,4-d]-pyrimidine (m.p.: 127°–129° C.) and piperazine.

M.p.: 201°–203° C. (ethanol).

Example 90

4-(1-Oxido-thiomorpholino)-2-piperazino-8-(3-trifluoromethylbenzyl-thio)-pyrimido-[5,4-d]-pyrimidine This compound was prepared analogous to Example 1 from 2-chloro-4-(1-oxido-thiomorpholino)-8-(3-trifluoromethylbenzyl-thio)-pyrimido-[5,4-d]-pyrimidine (m.p.: 211°–213° C.) and piperazine.

M.p.: 221°–222° C. (ethanol).

M.p. of the hydrochloride: 269°–271° C.

Example 91

8-(4-Methylbenzyl-thio)-4-(1-oxido-thiomorpholino)-2-piperazino-pyrimido-[5,4-d]-pyrimidine This compound was prepared analogous to Example 1 from 2-chloro-8-(4-methylbenzyl-thio)-4-(1-oxido-thiomorpholino)-pyrimido-[5,4-d]-pyrimidine (m.p.: 262°–264° C.) and piperazine.

M.p.: 215°–217° C. (methanol).

Example 92

8-(4-Methoxybenzyl-thio)-4-(1-oxido-thiomorpholino)-2-piperazino-pyrimido-[5,4-d]-pyrimidine This compound was prepared analogous to Example 1 from 2-chloro-8-(4-methoxybenzyl-thio)-4-(1-oxido-thiomorpholino)-pyrimido-[5,4-d]-pyrimidine (m.p.: 217°–219° C.) and piperazine.

M.p.: 236°–239° C.

Example 93

8-Mercapto-2-(N-methyl-piperazino)-4-morpholino-pyrimido-[5,4-d]-pyrimidine

This compound was prepared from 2-chloro-8-mercapto-4-morpholino-pyrimido-[5,4-d]-pyrimidine (m.p.: >300° C., decomp.) and N-methyl-piperazine by refluxing for 30 minutes in dioxane.

M.p.: 220°–222° C. (acetone).

M.p. of the hydrochloride: 263°–265° C. (decomp.).

Example 94

8-(2-Indanyl-thio)-4-morpholino-2-piperazino-pyrimido-[5,4-d]-pyrimidine

This compound was prepared analogous to Example 1 from 2-chloro-8-(2-indanyl-thio)-4-morpholino-pyrimido-[5,4-d]-pyrimidine (m.p.: 202°–205° C.) and piperazine.

M.p.: 228°–231° C.

Example 95

8-(α-Methyl-4-methylthiobenzyl-thio)-4-morpholino-2-piperazino-pyrimido-[5,4-d]-pyrimidine This compound was prepared analogous to Example 1 from 2-chloro-8-(α-methyl-4-methylthiobenzyl-thio)-4-morpholino-pyrimido-[5,4-d]-pyrimidine (m.p.: 146°–149° C.) and piperazine.
M.p.: 166°–169° C.

Example 96

8-(α-Methyl-4-methylthiobenzyl-thio)-4-(1-oxido-thiomorpholino)-2-piperazino-pyrimido-[5,4-d]-pyrimidine This compound was prepared analogous to Example 1 from 2-chloro-8-(α-methyl-4-methylthiobenzyl-thio)-4-(1-oxido-thiomorpholino)-pyrimido-[5,4-d]-pyrimidine (m.p.: 200°–202° C.) and piperazine.
M.p.: 158°–162° C.

Example 97

4-(1-Oxido-thiomorpholino)-2-piperazino-8-propylthio-pyrimido-[5,4-d]-pyrimidine This compound was prepared analogous to Example 1 from 2-chloro-4-(1-oxido-thiomorpholino)-8-propylthio-pyrimido-[5,4-d]-pyrimidine (m.p.: 209°–210° C.) and piperazine.
M.p.: 234°–236° C. (ethanol).

Example 98

4-(1-Oxido-thiomorpholino)-8-(3-phenylpropyl-thio)-2-piperazino-pyrimido-[5,4-d]-pyrimidine This compound was prepared analogous to Example 1 from 2-chloro-4-(1-oxido-thiomorpholino)-8-(3-phenylpropyl-thio)-pyrimido-[5,4-d]-pyrimidine (m.p.: 172°–174° C.) and piperazine.
M.p.: 167°–169° C. (ethanol).

Example 99

8-(2-Hydroxyethoxy)-4-(1-oxido-thiomorpholino)-2-piperazino-pyrimido-[5,4-d]-pyrimidine This compound was prepared analogous to Example 1 from 2-chloro-8-hydroxyethoxy-4-(1-oxido-thiomorpholino)-pyrimido-[5,4-d]-pyrimidine (m.p.: 235°–236° C.) and piperazine.
M.p.: 150°–153° C. (ethyl acetate).

Example 100

2-(N-Formyl-piperazino)-8-methylthio-4-(1-oxido-thiomorpholino)-pyrimido-[5,4-d]-pyrimidine This compound was prepared analogous to Example 3 from 2-chloro-8-methylthio-4-(1-oxido-thiomorpholino)-pyrimido-[5,4-d]-pyrimidine (m.p.: 260°–262° C.) and N-formyl-piperazine.
M.p.: 269°–271° C. (ethanol).

Example 101

2-(N-Formyl-piperazino)-4-(1-oxido-thiomorpholino)-8-phenethylthio-pyrimido-[5,4-d]-pyrimidine This compound was prepared analogous to Example 3 from 2-chloro-4-(1-oxido-thiomorpholino)-8-phenethylthio-pyrimido-[5,4-d]-pyrimidine (m.p.: 248°–250° C.) and piperazine in dioxane.
M.p.: 154°–156° C. (methanol).

Example 102

8-Benzylthio-4-morpholino-2-[N-(2-thenoyl)-piperazino]-pyrimido-[5,4-d]-pyrimidine This compound was prepared analogous to Example 6 from 8-benzylthio-4-morpholino-2-piperazino-pyrimido-[5,4-d]-pyrimidine (m.p.: 191°–193° C.) and thiophene-2-carboxylic acid chloride in dry pyridine.
M.p.: 210°–212° C. (ethanol/dioxane).

Example 103

8-Benzylthio-2-[N-(2-furoyl)-piperazino]-4-(1-oxido-thiomorpholino)-pyrimido-[5,4-d]-pyrimidine This compound was prepared analogous to Example 6 from 8-benzylthio-4-(1-oxido-thiomorpholino)-2-piperazino-pyrimido-[5,4-d]-pyrimidine (m.p.: 206°–208° C.) and furan-2-carboxylic acid chloride in dry pyridine.
M.p.: 220°–222° C. (ethanol/dioxane).

Example 104

8-Benzylthio-4-(1-oxido-thiomorpholino)-2-[N-(2-thenoyl)-piperazino]-pyrimido-[5,4-d]-pyrimidine This compound was prepared analogous to Example 6 from 8-benzylthio-4-(1-oxido-thiomorpholino)-2-piperazino-pyrimido-[5,4-d]-pyrimidine (m.p. 206°–208° C.) and thiophene-2-carboxylic acid chloride in dry pyridine.
M.p.: 205°–207° C. (ethanol/dioxane).

Example 105

2-[N-(2-Furoyl)-piperazino]-8-methylthio-4-(1-oxido-thiomorpholino)-pyrimido-[5,4-d]-pyrimidine This compound was prepared analogous to Example 6 from 8-methylthio-4-(1-oxido-thiomorpholino)-2-piperazino-pyrimido-[5,4-d]-pyrimidine (m.p.: 253°–255° C.) and furan-2-carboxylic acid chloride in acetone in the presence of pyridine.
M.p.: 278°–280° C. (ethanol/dioxane).

Example 106

2-[N-(2-Furoyl)-piperazino]-4-(1-oxido-thiomorpholino)-8-phenethylthio-pyrimido-[5,4-d]-pyrimidine This compound was prepared analogous to Example 6 from 4-(1-oxido-thiomorpholino)-8-phenethylthio-2-piperazino-pyrimido-[5,4-d]-pyrimidine (m.p.: 188°–190° C.) and furan-2-carboxylic acid chloride in acetone in the presence of pyridine.
M.p.: 210°–212° C. (ethanol).

Example 107

8-Benzylthio-2-(N-formylpiperazino)-4-morpholino-pyrimido-[5,4-d]-pyrimidine 0.7 ml (0.006 mol) of benzyl chloride were added dropwise to a solution of 1.8 gm (0.005 mol) of 2-(N-formylpiperazino)-8-mercapto-4-morpholino-pyrimido-[5,4-d]-pyrimidine (m.p. 250°–255° C.) in about 60 ml of 0.1N sodium hydroxide. After stirring the mixture at room temperature for one hour, the precipitated reaction product was suction-filtered off, washed with water and dried.
Yield: 2.0 gm (89% of theory).
After recrystallization from ethyl acetate the 8-benzylthio-2-(N-formylpiperazino)-4-morpholino-pyrimido-[5,4-d]-pyrimidine melted at 228°–230° C.

$C_{22}H_{25}N_7O_2S$ (451.6) Calc.: C—58.52%; H—5.58%; N—21.71%; S—7.10% Found: C—58.55%; H—5.51%; N—21.45%; S—6.98%.

Example 108

4-Morpholino-8-(1-naphthylmethyl-thio)-2-piperazino-pyrimido-[5,4-d]-pyrimidine

This compound was prepared analogous to Example 1 from 2-chloro-4-morpholino-8-(1-naphthylmethyl-thio)-pyrimido [5,4-d]-pyrimidine (m.p.: 206°–209° C.) and piperazine.

M.p.: 239°–241° C.

Example 109

8-(1-Naphthylmethyl-thio)-4-(1-oxido-thiomorpholino)-2-piperazino-pyrimido-[5,4-d]-pyrimidine This compound was prepared analogous to Example 1 from 2-chloro-8-(1-naphthylmethyl-thio)-4-(oxido-thiomorpholino)-pyrimido-[5,4-d]-pyrimidine (m.p.: 212°–215° C.) and piperazine.

M.p.: 246°–248° C.

Example 110

8-(Furfuryl-thio)-4-morpholino-2-piperazino-pyrimido-[5,4-d]-pyrimidine

This compound was prepared analogous to Example 1 from 2-chloro-8-(furfuryl-thio)-4-morpholino-pyrimido-[5,4-d]-pyrimidine (m.p.: 139°–141° C.) and piperazine.

M.p.: 179°–181° C.

Example 111

8-(Furfuryl-thio)-4-(1-oxido-thiomorpholino)-2-piperazino-pyrimido-[5,4-d]-pyrimidine This compound was prepared analogous to Example 1 from 2-chloro-8-(furfuryl-thio)-4-(1-oxido-thiomorpholino)-pyrimido-[5,4-d]-pyrimidine (m.p.: 173°–175° C.) and piperazine.

M.p.: 208°–211° C.

Example 112

4-Morpholino-8-(3-nitrobenzyl-thio)-2-piperazino-pyrimido-[5,4-d]-pyrimidine

This compound was prepared analogous to Example 1 from 2-chloro-4-morpholino-8-(3-nitrobenzyl-thio)-pyrimido-[5,4-d]-pyrimidine (m.p.: 153°–156° C.) and piperazine.

M.p.: 173°–175° C. (ethyl acetate).

Example 113

4-Morpholino-8-(4-nitrobenzyl-thio)-2-piperazino-pyrimido-[5,4-d]-pyrimidine

This compound was prepared analogous to Example 1 from 2-chloro-4-morpholino-8-(4-nitrobenzyl-thio)-pyrimido-[5,4-d]-pyrimidine (m.p. 187°–190° C.) and piperazine.

M.p.: 190°–192° C. (ethyl acetate).

Example 114

8-(3,4-Methylenedioxybenzyl-thio)-4-morpholino-2-piperazino-pyrimido-[5,4-d]-pyrimidine This compound was prepared analogous to Example 1 from 2-chloro-8-(3,4-methylenedioxybenzyl-thio)-4-morpholino-pyrimido-[5,4-d]-pyrimidine (m.p.: 200°–202° C.) and piperazine.

M.p.: 208°–210° C.

Example 115

2-(N-Formyl-piperazino)-8-mercapto-4-morpholino-pyrimido-[5,4-d]-pyrimidine

This compound was prepared analogous to Example 93 from 2-chloro-8-mercapto-4-morpholino-pyrimido-[5,4-d]-pyrimidine (m.p.: >300° C., decomp.) and N-formyl-piperazine.

M.p.: 250°–255° C. (decomp.).

Example 116

8-(4-Fluorobenzyl-thio)-2-(N-formyl-piperazino)-4-(1-oxido-thiomorpholino)-pyrimido-[5,4-d]-pyrimidine This compound was prepared analogous to Example 93 from 2-chloro-8-(4-fluorobenzyl-thio)-4-(1-oxido-thiomorpholino)-pyrimido-[5,4-d]-pyrimidine (m.p.: 192°–194° C.) and N-formyl-piperazine in dioxane.

M.p.: 160°–163° C.

Example 117

2-(N-Formyl-piperazino)-8-mercapto-4-(1-oxido-thiomorpholino)-pyrimido-[5,4-d]-pyrimidine This compound was prepared analagous to Example 93 from 2-chloro-8-mercapto-4-(1-oxido-thiomorpholino)-pyrimido-[5,4-d]-pyrimidine (m.p.: >280° C., decomp.) and N-formyl-piperazine.

M.p.: 230°–233° C. (decomp.).

Example 118

8-(N-Benzyl-methylamino)-4-(1-oxido-thiomorpholino)-2-piperazino-pyrimido-[5,4-d]-pyrimidine 8.1 gm (0.002 mol) of 8-(N-benzyl-methylamino)-2-chloro-4-(1-oxido-thiomorpholino)-pyrimido-[5,4-d]-pyrimidine (m.p.: 158°–160° C.) were refluxed for 30 minutes with 6.9 gm (0.08 mol) of anhydrous piperazine in 150 ml of dioxane. The solvent was then distilled off, and the residue was taken up in about 600 ml of water. After standing for a short time, the reaction product was suction-filtered off, washed with water and dried at about 60° C.

Yield: 9.1 gm (95% of theory).

For purification, the crude product was precipitated from 0.2N hydroxhloric acid with ammonia and recrystallized from methanol. The 8-(N-benzyl-methylamino)-4-(1-oxido-thiomorpholino)-2-piperazino-pyrimido-[5,4-d]-pyrimidine thus obtained melted at 214°–215° C.

$C_{22}H_{28}N_8OS$ (452.6) Calc.: C—58.38%; H—6.24%; N—24.76%; S—7.08% Found: C—58.22%; H—6.45%; N—24.68%; S—7.22%.

The same compound was obtained by heating 8-(N-benzyl-methylamino)-4-(1-oxido-thiomorpholino)-2-phenoxy-pyrimido-[5,4-d]-pyrimidine [m.p.: 187°–189° C.; prepared from 8-(N-benzyl-methylamino)-2-chloro-4-(1-oxido-thiomorpholino)-pyrimido-[5,4-d]-pyrimidine and sodium phenolate in phenol] with piperazine at about 110° C. for 2 hours; or by oxidizing 8-(N-benzyl-methylamino)-2-piperazino-4-thiomorpholino-pyrimido-[5,4-d]-pyrimidine (m.p.: 108°–110° C.) with hydrogen peroxide in glacial acetic acid or with potassium permanganate in dilute hydrochloric acid while cooling. By reacting the 8-(N-benzyl-methylamino)-4-(1-oxido-thiomorpholino)-2-piperazino-pyrimido-[5,4-d]-pyrimidine with an excess of the corresponding acid in isopropanol the following salts were prepared.

M.p. of the succinate: 195°–198° C.,

M.p. of the maleate: 135°–138° C.,
M.p. of the tartrate: 195°–200° C. (decomp.),
M.p. of the tosylate: 270°–273° C. (decomp.).

Example 119

8-Diethanolamino-4-morpholino-2-piperazino-pyrimido-[5,4-d]-pyrimidine 8.9 gm (0.025 mol) of 2-chloro-8-diethanolamino-4-morpholino-pyrimido-[5,4-d]-pyrimidine (m.p.: 129°–131° C.) were heated with 21.5 gm (0.25 mol) of piperazine for one hour to about 120° C. The obtained melt was taken up in about 200 ml of water. After standing for a while, a yellowish precipitate was obtained which was suction-filtered off, washed with water and dried at 70° C.

Yield: 8.8 gm (87% of theory).

After reprecipitation from 0.1N hydrochloric acid with ammonia the 8-diethanolamine-4-morpholino-2-piperazino-pyrimido-[5,4-d]-pyrimidine melted at 188°–190° C.

$C_{18}H_{28}N_8O_3$ (404.5) Calc.: C—53.45%; H—6.98%; N—27.70% Found: C—53.20%; H—7.03%; N—27.40%.

Example 120

8-Benzylamino-4-(1-oxido-thiomorpholino)-2-piperazino-pyrimido-[5,4-d]-pyrimidine 1.9 gm (0.005 mol) of 8-methylthio-4-(1-oxido-thiomorpholino)-2-piperazino-pyrimido-[5,4-d]-pyrimidine (m.p.: 253°–255° C.) were heated with 25 ml of benzylamine for about one hour at 150° C. Subsequently, the excess amine was largely distilled off in vacuo, the residue was taken up in about 150 ml of water, and the solution was adjusted to pH 7 with dilute hydrochloric acid. The precipitated reaction product was suction-filtered off, washed with water and dried.

Yield: 1.6 gm (73% of theory).

After recrystallization from ethanol/water the 8-benzylamino-4-(1-oxido-thiomorpholino)-2-piperazino-pyrimido-[5,4-d]-pyrimidine melted at 229°–232° C.

$C_{21}H_{26}N_8OS$ (438.6) Calc.: C—57.51%; H—5.96%; N—25.55%; S—7.32% Found: C—57.60%; H—6.07%; N—25.65%; S—7.33%.

Example 121

8-Amino-4-morpholino-2-piperazino-pyrimido-[5,4-d]-pyrimidine

This compound was prepared analogous to Example 118 from 8-amino-2-chloro-4-morpholino-pyrimido-[5,4-d]-pyrimidine (m.p.: 206°–208° C.) and piperazine.

M.p.: 260°–263° C.

Example 122

8-Amino-4-(1-oxido-thiomorpholino)-2-piperazino-pyrimido-[5,4-d]-pyrimidine

This compound was prepared analogous to Example 118 from 8-amino-2-chloro-4-(1-oxido-thiomorpholino)-pyrimido-[5,4-d]-pyrimidine (m.p.: 270°–272° C., decomp.) and piperazine.

M.p.: 248°–250° C. (methanol).

Example 123

8-Methylamino-4-(1-oxido-thiomorpholino)-2-piperazino-pyrimido-[5,4-d]-pyrimidine This compound was prepared analogous to Example 118 from 2-chloro-8-methylamino-4-(1-oxido-thiomorpholino)-pyrimido-[5,4-d]-pyrimidine (m.p.: 278°–280° C.) and piperazine in dioxane at 80° C.

M.p.: 257°–259° C.

Example 124

4-(1-Oxido-thiomorpholino)-2-piperazino-8-propylamino-pyrimido-[5,4-d]-pyrimidine This compound was prepared analogous to Example 123 from 2-chloro-4-(1-oxido-thiomorpholino)-8-propylamino-pyrimido-[5,4-d]-pyrimidine (m.p.: 174°–176° C.) and piperazine.

M.p.: 198°–200° C.

Example 125

8-Isopropylamino-4-(1-oxido-thiomorpholino)-2-piperazino-pyrimido-[5,4-d]-pyrimidine This compound was prepared analogous to Example 123 from 2-chloro-8-isopropylamino-4-(1-oxido-thiomorpholino)-pyrimido-[5,4-d]-pyrimidine (m.p.: 210°–212° C.) and piperazine.

M.p.: 179°–181° C. (ethyl acetate).

Example 126

8-Butylamino-4-(1-oxido-thiomorpholino)-2-piperazino-pyrimido-[5,4-d]-pyrimidine This compound was prepared analogous to Example 123 from 8-butylamino-2-chloro-4-(1-oxido-thiomorpholino)-pyrimido-[5,4-d]-pyrimidine (m.p.: 179°–181° C.) and piperazine.

M.p.: 138°–140° C. (dioxane).

Example 127

8-Isoamylamino-4-(1-oxido-thiomorpholino)-2-piperazino-pyrimido-[5,4-d]-pyrimidine This compound was prepared analogous to Example 123 from 2-chloro-8-isoamylamino-4-(1-oxido-thiomorpholino)-pyrimido-[5,4-d]-pyrimidine (m.p.: 176°–178° C.) and piperazine.

M.p.: 206°–208° C. (methanol/water).

Example 128

8-Octylamino-4-(1-oxido-thiomorpholino)-2-piperazino-pyrimido-[5,4-d]-pyrimidine This compound was prepared analogous to Example 123 from 2-chloro-8-octylamino-4-(1-oxido-thiomorpholino)-pyrimido-[5,4-d]-pyrimidine (m.p.: 145°–147° C.) and piperazine.

M.p.: 142°–144° C. (ethyl acetate).

Example 129

8-Cyclohexylamino-4-(1-oxido-thiomorpholino)-2-piperazino-pyrimido-[5,4-d]-pyrimidine This compound was prepared analogous to Example 123 from 2-chloro-8-cyclohexylamino-4-(1-oxido-thiomorpholino)-pyrimido-[5,4-d]-pyrimidine (m.p.: 207°–209° C.) and piperazine.

M.p.: 207°–209° C.

Example 130

8-Diethylamino-4-(1-oxido-thiomorpholino)-1-piperazino-pyrimido-[5,4-d]-pyrimidine This compound was prepared analogous to Example 123 from 2-chloro-8-diethylamino-4-(1-oxido-thiomorpholino)-pyrimido-[5,4-d]-pyrimidine (m.p.: 184°–186° C.) and piperazine.

M.p.: 185°–187° C. (ethyl acetate).

Example 131

8-Dibutylamino-4-(1-oxido-thiomorpholino)-2-piperazino-pyrimido-[5,4-d]-pyrimidine This compound was prepared analogous to Example 123 from 2-chloro-8-dibutylamino-4-(1-oxido-thiomorpholino)-pyrimido-[5,4-d]-pyrimidine (m.p.: 187°–189° C.) and piperazine.

M.p.: 171°–173° C. (ethyl acetate).

Example 132

4-(1-Oxido-thiomorpholino)-2-piperazino-8-piperidino-pyrimido-[5,4-d]-pyrimidine This compound was prepared analogous to Example 123 from 2-chloro-4-(1-oxido-thiomorpholino)-8-piperidino-pyrimido-[5,4-d]-pyrimidine (m.p.: 203°–205° C.) and piperazine.

M.p.: 115°–117° C. (ethyl acetate).

Example 133

4-(1-Oxido-thiomorpholino)-2-piperazino-8-thiomorpholino-pyrimido-[5,4-d]-pyrimidine This compound was prepared analogous to Example 118 from 2-chloro-4-(1-oxido-thiomorpholino)-8-thiomorpholino-pyrimido-[5,4-d]-pyrimidine (m.p.: 229°–231° C.) and piperazine.

M.p.: 207°–209° C. (dioxane).

Example 134

8-Morpholino-4-(1-oxido-thiomorpholino)-2-piperazino-pyrimido-[5,4-d]-pyrimidine This compound was prepared analogous to Example 118 from 2-chloro-8-morpholino-4-(1-oxido-thiomorpholino)-pyrimido-[5,4-d]-pyrimidine (m.p.: 232°–233° C.) and piperazine.

M.p.: 168°–171° C.

Example 135

8-Benzylamino-4-morpholino-2-piperazino-pyrimido-[5,4-d]-pyrimidine

This compound was prepared analogous to Example 118 from 8-benzylamino-2-chloro-4-morpholino-pyrimido-[5,4-d]-pyrimidine (m.p.: 139°–141° C.) and piperazine.

M.p.: 154°–157° C.

Example 136

8-Benzylamino-2-piperazino-4-thiomorpholino-pyrimido-[5,4-d]-pyrimidine

This compound was prepared analogous to Example 118 from 8-benzylamino-2-chloro-4-thiomorpholino-pyrimido-[5,4-d]-pyrimidine (m.p.: 94°–96° C.) and piperazine.

M.p.: 109°–111° C.

Example 137

8-Benzylamino-4-(1-oxido-thiomorpholino)-2-piperazino-pyrimido-[5,4-d]-pyrimidine This compound was prepared analogous to Example 118 from 8-benzylamino-2-chloro-4-(1-oxido-thiomorpholino)-pyrimido-[5,4-d]-pyrimidine (m.p.: 232°–233° C.) and piperazine in dioxane at 70° C.

M.p.: 229°–232° C. (ethanol/water).

The same substance was also obtained from 8-benzylamino-2-piperazino-4-thiomorpholino-pyrimido-[5,4-d]-pyrimidine by oxidation with sodium metaperiodate in methanol under reflux.

Example 138

8-Benzylamino-4-(1,1-dioxido-thiomorpholino)-2-piperazino-pyrimido-[5,4-d]-pyrimidine This compound was prepared analogous to Example 118 from 8-benzylamino-2-chloro-4-(1,1-dioxido-thiomorpholino)-pyrimido-[5,4-d]-pyrimidine (m.p.: 213°–215° C.) and piperazine.

M.p.: 203°–205° C.

The same substance was also obtained from 8-benzylamino-4-(1-oxido-thiomorpholino)-2-piperazino-pyrimido-[5,4-d]-pyrimidine by oxidation with potassium permanganate in dilute hydrochloric acid.

Example 139

4-Morpholino-8-phenethylamino-2-piperazino-pyrimido-[5,4-d]-pyrimidine

This compound was prepared analogous to Example 118 from 2-chloro-4-morpholino-8-phenethylamino-pyrimido-[5,4-d]-pyrimidine (m.p.: 132°–134° C.) and piperazine.

M.p.: 125°–127° C. (cyclohexane).

Example 140

4-(1-Oxido-thiomorpholino)-8-phenethylamino-2-piperazino-pyrimido-[5,4-d]-pyrimidine This compound was prepared analogous to Example 118 from 2-chloro-4-(1-oxido-thiomorpholino)-8-phenethylamino-pyrimido-[5,4-d]-pyrimidine (m.p.: 198°–200° C.) and piperazine.

M.p.: 213°–215° C. (methanol).

Example 141

4-(1-Oxido-thiomorpholino)-8-(3-phenylpropyl-amino)-2-piperazino-pyrimido-[5,4-d]-pyrimidine This compound was prepared analogous to Example 118 from 2-chloro-4-(1-oxido-thiomorpholino)-8-(3-phenylpropyl-amino)-pyrimido-[5,4-d]-pyrimidine (m.p.: 152°–154° C.) and piperazine.

M.p.: 210°–212° C. (methanol).

Example 142

4-(1-Oxido-thiomorpholino)-8-(D-1-phenylethyl-amino)-2-piperazino-pyrimido-[5,4-d]-pyrimidine This compound was prepared analogous to Example 118 from 2-chloro-4-(1-oxido-thiomorpholino)-8-(D-1-phenylethyl-amino)-pyrimido-[5,4-d]-pyrimidine (m.p.: 167°–169° C.) and piperazine.

M.p.: 115°–120° C.

Example 144

8-(N-Benzyl-methylamino)-4-morpholino-2-piperazino-pyrimido-[5,4-d]-pyrimidine

This compound was prepared analogous to Example 118 from 8-(N-benzyl-methylamino)-2-chloro-4-morpholino-pyrimido-[5,4-d]-pyrimidine (m.p.: 121°–123° C.) and piperazine.

M.p.: 147°–149° C.

Example 145

8-(N-Benzyl-methylamino)-2-piperazino-4-thiomorpholino-pyrimido-[5,4-d]-pyrimidine This compound was prepared analogous to Example 118 from 8-(N-benzyl-methyl-amino)-2-chloro-4-thiomorpholino-pyrimido-[5,4-d]-pyrimidine and piperazine.

M.p.: 108°–110° C. (methanol).

Example 146

8-(N-Ethyl-benzylamino)-4-(1-oxido-thiomorpholino)-2-piperazino-pyrimido-[5,4-d]-pyrimidine This compound was prepared analogous to Example 118 from 8-(N-ethyl-benzylamino)-2-chloro-4-(1-oxido-thiomorpholino)-pyrimido-[5,4-d]-pyrimidine (m.p.: 163°–165° C.) and piperazine.

M.p.: 174°–176° C. (methanol/water).

Example 147

8-(N-Benzyl-propylamino)-4-(1-oxido-thiomorpholino)-2-piperzino-pyrimido-[5,4-d]-pyrimidine This compound was prepared analogous to Example 118 from 8-(N-benzyl-propylamino)-2-chloro-4-(1-oxido-thiomorpholino)-pyrimido-[5,4-d]-pyrimidine (m.p.: 183°–184° C.) and piperazine.

M.p.: 158°–160° C. (methanol/water).

Example 148

8-(N-Benzyl-butylamino)-4-(1-oxido-thiomorpholino)-2-piperazino-pyrimido-[5,4-d]-pyrimdine This compound was prepared analogous to Example 118 from 8-(N-benzyl-butylamino)-2-chloro-4-(1-oxido-thiomorpholino)-pyrimido-[5,4-d]-pyrimidine (m.p.: 153°–155° C.) and piperazine.

M.p.: 154°–156° C.

Example 149

8-Anilino-4-morpholino-2-piperazino-pyrimido-[5,4-d]-pyrimidine

This compound was prepared analogous to Example 118 from 8-anilino-2-chloro-4-morpholino-pyrimido-[5,4-d]-pyrimidine (m.p.: 193°–195° C.) and piperazine.

M.p.: 184°–186° C. (methanol).

Example 150

8-Anilino-4-(1-oxido-thiomorpholino)-2-piperazino-pyrimido-[5,4-d]-pyrimidine

This compound was prepared analogous to Example 118 from 8-anilino-2-chloro-4-(1-oxido-thiomorpholino)-pyrimido-[5,4-d]-pyrimidine (m.p.: 230°–232° C.) and piperazine.

M.p.: 205°–210° C. (ethanol).

Example 151

8-(N-Methyl-anilino)-4-morpholino-2-piperazino-pyrimido-[5,4-d]-pyrimidine

This compound was prepared analogous to Example 118 from 2-chloro-8-(N-methylanilino)-4-morpholino-pyrimido-[5,4-d]-pyrimidine (m.p.: 150°–152° C.) and piperazine.

M.p.: 212°–215° C.

Example 152

8-(N-Methyl-anilino)-4-(1-oxido-thiomorpholino)-2-piperazino-pyrimido-[5,4-d]-pyrimidine This compound was prepared analogous to Example 118 from 2-chloro-8-(N-methyl-anilino)-4-(1-oxido-thiomorpholino)-pyrimido-[5,4-d]-pyrimidine (m.p.: 237°–239° C.) and piperazine.

M.p.: 257°–259° C. (dioxane).

Example 153

8-(2-Hydroxyethyl-amino)-4-(1-oxido-thiomorpholino)-2-piperazino-pyrimido-[5,4-d]-pyrimidine This compound was prepared analogous to Example 118 from 2-chloro-8-(2-hydroxyethyl-amino)-4-(1-oxido-thiomorpholino)-pyrimido-[5,4-d]-pyrimidine (m.p.: 227°–229° C.) and piperazine.

M.p.: 228°–230° C.

EXAMPLE 154

8-(4-Hydroxybutyl-amino)-4-(1-oxido-thiomorpholino)-2-piperazino-pyrimido-[5,4-d]-pyrimidine This compound was prepared analogous to Example 118 from 2-chloro-8-(4-hydroxybutyl-amino)-4-(1-oxido-thiomorpholino)-pyrimido-[5,4-d]-pyrimidine (m.p.: 179°–181° C.) and piperazine.

M.p.: 187°–189° C. (ethanol/ethyl acetate).

Example 155

8-Diethanolamino-2-piperazino-4-thiomorpholino-pyrimido-[5,4-d]-pyrimidine

This compound was prepared analogous to Example 119 from 2-chloro-8-diethanol-amino-4-thiomorpholino-pyrimido-[5,4-d]-pyrimidine (m.p.: 121°–123° C.) and piperazine.

M.p.: 192°–195° C.

Example 156

8-Diethanolamino-4-(1-oxido-thiomorpholino)-2-piperazino-pyrimido-[5,4-d]-pyrimidine This compound was prepared analogous to Example 118 from 2-chloro-8-diethanol-amino-4-(1-oxido-thiomorpholino)-pyrimido-[5,4-d]-pyrimidine (m.p.: 187°–189° C.) and piperazine.

M.p.: 226°–228° C. (ethanol).

Example 157

8-Diisopropanolamino-4-(1-oxido-thiomorpholino)-2-piperazino-pyrimido-[5,4-d]-pyrimidine This compound was prepared analogous to Example 118 from 2-chloro-8-diisopropanolamino-4-(1-oxido-thiomorpholino)-pyrimido-[5,4-d]-pyrimidine (m.p.: 205°–208° C.) and piperazine.

M.p.: 222°–225° C. (ethanol).

Example 158

8-[N-(2-Hydroxyethyl)-N-(2-methoxyethyl)-amino]-4-(1-oxido-thiomorpholino)-2-piperazino-pyrimido-[5,4-d]-pyrimidine This compound was prepared analogous to Example 118 from 2-chloro-8-[N-(2-hydroxyethyl)-N-(2-methoxyethyl)-amino]-4-(1-oxido-thiomorpholino)-pyrimido-[5,4-d]-pyrimidine (m.p.: 143°–145° C.) and piperazine.

M.p.: 143°–146° C. (ethyl acetate).

Example 159

8-[N-Benzyl-2-hydroxyethyl-amino]-4-(1-oxido-thiomorpholino)-2-piperazino-pyrimido-[5,4-d]-pyrimidine This compound was prepared analogous to Example 118 from 8-[N-benzyl-N-(2-hydroxyethyl)-amino]-2-chloro-4-(1-oxido-thiomorpholino)-pyrimido-[5,4-d]-pyrimidine (m.p.: 153°–155° C.) and piperazine.
M.p.: 138°–141° C.

Example 160

4-(1-Oxido-thiomorpholino)-8-(3-picolyl-amino)-2-piperazino-pyrimido-[5,4-d]-pyrimidine This compound was prepared analogous to Example 118 from 2-chloro-4-(1-oxido-thiomorpholino)-8-(3-picolylamino)-pyrimido-[5,4-d]-pyrimidine (m.p.: 227°–229° C.) and piperazine.
M.p.: 267°–269° C.

Example 161

8-[N-Methyl-N-(3-picolyl)-amino]-4-(1-oxido-thiomorpholino)-2-piperazino-pyrimido-[5,4-d]-pyrimidine This compound was prepared analogous to Example 118 from 2-chloro-8-[N-methyl-N-(3-picolyl)-amino]-4-(1-oxido-thiomorpholino)-pyrimido-[5,4-d]-pyrimidine (m.p.: 154°–156° C.) and piperazine.
M.p.: 191°–194° C.

Example 162

8-Furfurylamino-4-(1-oxido-thiomorpholino)-2-piperazino-pyrimido-[5,4-d]-pyrimidine This compound was prepared analogous to Example 118 from 2-chloro-8-furfurylamino-4-(1-oxido-thiomorpholino)-pyrimido-[5,4-d]-pyrimidine (m.p.: 203°–205° C.) and piperazine in dioxane at 80° C.
M.p.: 219°–221° C.

Example 163

8-Benzylamino-2-(N-methyl-piperazino)-4-(1-oxido-thiomorpholino-pyrimido-[5,4-d]-pyrimidine This compound was prepared analogous to Example 118 from 8-benzylamino-2-chloro-4-(1-oxido-thiomorpholino)-pyrimido-[5,4-d]-pyrimidine (m.p.: 232°–233° C.) and N-methyl-piperazine.
M.p.: 203°–205° C. (ethanol).

Example 164

8-Benzylamino-2-(N-hydroxyethyl-piperazino)-4-morpholino-pyrimido-[5,4-d]-pyrimidine This compound was prepared analogous to Example 118 from 8-benzylamino-2-chloro-4-morpholino-pyrimido-[5,4-d]-pyrimidine (m.p.: 139°–141° C.) and N-hydroxyethyl-piperazine in dioxane at 70° C.
M.p.: 161°–163° C. (cyclohexane/ethyl acetate).

Example 165

8-Benzylamino-2-(N-hydroxyethyl-piperazino)-4-(1-oxido-thiomorpholino)-pyrimido-[5,4-d]-pyrimidine This compound was prepared analogous to Example 118 from 8-benzylamino-2-chloro-4-(1-oxido-thiomorpholino)-pyrimido-[5,4-d]-pyrimidine (m.p.: 232°–233° C.) and N-hydroxyethyl-piperazine.
M.p.: 184°–186° C. (ethanol).

Example 166

8-(N-Benzyl-methylamino)-2-(N-hydroxyethyl-piperazino)-4-(1-oxido-thiomorpholino)-pyrimido-[5,4-d]-pyrimidine This compound was prepared analogous to Example 118 from 8-(N-benzyl-methylamino)-2-chloro-4-(1-oxido-thiomorpholino)-pyrimido-[5,4-d]-pyrimidine (m.p.: 158°–160° C.) and N-hydroxyethyl-piperazine.
M.p.: 126°–130° C. (ethyl acetate).

Example 167

2-(N-Hydroxyethyl-piperazino)-4-(1-oxido-thiomorpholino)-8-phenethylamino-pyrimido-[5,4-d]-pyrimidine This compound was prepared analogous to Example 118 from 2-chloro-4-(1-oxido-thiomorpholino)-8-phenethylamino-pyrimido-[5,4-d]-pyrimidine (m.p.: 198°–200° C.) and N-hydroxyethyl-piperazine.
M.p.: 166°–168° C. (ethyl acetate).

Example 168

8-(4-Fluorobenzyl-amino)-4-(1-oxido-thiomorpholino)-2-piperazino-pyrimido-[5,4-d]-pyrimidine This compound was prepared analogous to Example 118 from 2-chloro-8-(4-fluorobenzylamino)-4-(1-oxido-thiomorpholino)-pyrimido-[5,4-d]-pyrimidine (m.p.: 210°–212° C.) and piperazine in dioxane at 80° C.
M.p.: 148°–150° C.

Example 169

8-(4-Chlorobenzyl-amino)-4-(1-oxido-thiomorpholino)-2-piperazino-pyrimido-[5,4-d]-pyrimidine This compound was prepared analogous to Example 168 from 2-chloro-8-(4-chlorobenzyl-amino)-4-(1-oxido-thiomorpholino)-pyrimido-[5,4-d]-pyrimidine (m.p.: 216°–218° C.) and piperazine.
M.p.: 227°–229° C. (dioxane).

Example 170

8-(3-Chlorobenzyl-amino)-4-(1-oxido-thiomorpholino)-2-piperazino-pyrimido-[5,4-d]-pyrimidine This compound was prepared analogous to Example 168 from 2-chloro-8-(3-chlorobenzyl-amino)-4-(1-oxido-thiomorpholino)-pyrimido-[5,4-d]-pyrimidine (m.p.: 239°–241° C.) and piperazine.
M.p.: 208°–210° C.) dioxane.

Example 171

8-(2-Chlorobenzyl-amino)-4-(1-oxido-thiomorpholino)-2-piperazino-pyrimido-[5,4-d]-pyrimidine This compound was prepared analogous to Example 168 from 2-chloro-8-(2-chlorobenzyl-amino)-4-(1-oxido-thiomorpholino)-pyrimido-[5,4-d]-pyrimidine (m.p. 238°–240° C.) and piperazine.
M.p.: 193°–195° C. (dioxane).

Example 172

8-(4-Methylbenzyl-amino)-4-(1-oxido-thiomorpholino)-2-piperazino-pyrimido-[5,4-d]-pyrimidine This compound was prepared analogous to Example 168 from 2-chloro-8-(4-methylbenzyl-amino)-4-(1-oxido-thiomorpholino)-pyrimido-[5,4-d]-pyrimidine (m.p.: 185°–187° C.) and piperazine.
M.p.: 172°–174° C. (methanol).

Example 173

8-(3,4-Dichlorobenzyl-amino)-4-(1-oxido-thiomorpholino)-2-piperazino-pyrimido-[5,4-d]-pyrimidine This compound was prepared analogous to Example 168 from 2-chloro-8-(3,4-dichlorobenzyl-amino)-4-(1-oxido-thiomorpholino)-pyrimido-[5,4-d]-pyrimidine (m.p.: 259°–261° C.) and piperazine.
M.p.: 201°–203° C.

Example 174

8-(2,4-Dichlorobenzyl-amino)-4-(1-oxido-thiomorpholino)-2-piperazino-pyrimido-[5,4-d]-pyrimidine This compound was prepared analogous to Example 168 from 2-chloro-8-(2,4-dichlorobenzyl-amino)-4-(1-oxido-thiomorpholino)-pyrimido-[5,4-d]-pyrimidine (m.p.: 196°–198° C.) and piperazine.
M.p.: 235°–237° C. (dioxane).

Example 175

8-(3,4-Dimethoxybenzyl-amino)-4-(1-oxido-thiomorpholino)-2-piperazino-pyrimido-[5,4-d]-pyrimidine This compound was prepared analogous to Example 168 from 2-chloro-8-(3,4-dimethoxybenzyl-amino)-4-(1-oxido-thiomorpholino)-pyrimido-[5,4-d]-pyrimidine (m.p.: 218°–220° C.) and piperazine.
M.p.: 198°–200° C. (dioxane).

Example 176

8-(3,4-Methylenedioxybenzyl-amino)-4-(1-oxido-thiomorpholino)-2-piperazino-pyrimido-[5,4-d]-pyrimidine This compound was prepared analogous to Example 168 from 2-chloro-8-(3,4-methylenedioxybenzyl-amino)-4-(1-oxido-thiomorpholino)-pyrimido-[5,4-d]-pyrimidine (m.p.: 239°–241° C.) and piperazine.
M.p.: 233°–235° C. (ethyl acetate/dioxane).

Example 177

8-(3,4-Dimethoxyphenethyl-amino)-4-(1-oxido-thiomorpholino)-2-piperazino-pyrimido-[5,4-d]-pyrimidine This compound was prepared analogous to Example 118 from 2-chloro-8-(3,4-dimethoxyphenethyl-amino)-4-(1-oxido-thiomorpholino)-pyrimido-[5,4-d]-pyrimidine (m.p.: 214°–216° C.) and piperazine.
M.p.: 166°–167° C. (methanol).

Example 178

8-[N-(3,4-Dimethoxyphenethyl)-methylamino]-4-(1-oxido-thiomorpholino)-2-piperazino-pyrimido-[5,4-d]-pyrimidine This compound was prepared analogous to Example 118 from 2-chloro-8-[N-(3,4-dimethoxyphenethyl)-methylamino]-4-(1-oxido-thiomorpholino)-pyrimido-[5,4-d]-pyrimidine (m.p.: 178°–179° C.) and piperazine.
M.p.: 145°–147° C. (ethyl acetate).

Example 179

8-(4-Ethoxy-anilino)-4-(1-oxido-thiomorpholino)-2-piperazino-pyrimido-[5,4-d]-pyrimidine This compound was prepared analogous to Example 118 from 8-(4-ethoxy-anilino)-2-chloro-4-(1-oxido-thiomorpholino)-pyrimido-[5,4-d]-pyrimidine (m.p.: 237°–240° C.) and piperazine.
M.p.: 215°–217° C. (ethanol).

Example 180

4-(1-Oxido-thiomorpholino)-2-piperazino-8-(3-trifluoromethyl-anilino)-pyrimido-[5,4-d]-pyrimidine This compound was prepared analogous to Example 118 from 2-chloro-4-(1-oxido-thiomorpholino)-8-(3-trifluoromethyl-anilino)-pyrimido-[5,4-d]-pyrimidine (m.p.: 215°–218° C.) and piperazine.
M.p.: 263°–266° C. (dioxane).

Example 181

2-(N-Formyl-piperazino)-8-morpholino-4-(1-oxido-thiomorpholino)-pyrimido-[5,4-d]-pyrimidine This compound was prepared analogous to Example 119 from 2-chloro-8-morpholino-4-(1-oxido-thiomorpholino)-pyrimido-[5,4-d]-pyrimidine (m.p.: 232°–233° C.) and N-formyl-piperazine at 100° C.
M.p.: 189°–190° C. (methanol/water).

Example 182

8-Amino-2-(N-formyl-piperazino)-4-(1-oxido-thiomorpholino)-pyrimido-[5,4-d]-pyrimidine This compound was prepared analogous to Example 181 from 8-amino-2-chloro-4-(1-oxido-thiomorpholino)-pyrimido-[5,4-d]-pyrimidine (m.p.: 270°–272° C., decomp.) and N-formyl-piperazine at 130° C.
M.p.: 278°–280° C.

Example 183

8-Benzylamino-2-(N-formyl-piperazino)-4-thiomorpholino-pyrimido-[5,4-d]-pyrimidine This compound was prepared analogous to Example 181 from 8-benzylamino-2-chloro-4-thiomorpholino-pyrimido-[5,4-d]-pyrimidine (m.p.: 94°–96° C. and N-formyl-piperazine.
M.p.: 187°–189° C.

Example 184

8-Benzylamino-2-(N-formylpiperazino)-4-)1-oxido-thiomorpholino-pyrimido-[5,4-d]-pyrimidine This compound was prepared analogous to Example 181 from 8-benzylamino-2-chloro-4-(1-oxido-thiomorpholino)-pyrimido-[5,4-d]-pyrimidine (m.p.: 232°–233° C.) and N-formyl-piperazine.
M.p.: 152°–155° C. (ethanol/water).

The same substance was also obtained from 8-amino-2-(N-formyl-piperazino)-4-(1-oxido-thiomorpholino)-pyrimido-[5,4-d]-pyrimidine by reaction with benzyl chloride and potassium tert. butylate in dimethyl sulfoxide.

Example 185

8-(N-Benzyl-methylamino)-2-(N-formyl-piperazino)-4-(1-oxido-thiomorpholino)-pyrimido-[5,4-d]-pyrimidine This compound was prepared analogous to Example 181 from 8-(N-benzyl-methylamino)-2-chloro-4-(1-oxido-thiomorpholino)-pyrimido-[5,4-d]-pyrimidine (m.p.: 158°–160° C.) and N-formyl-piperazine.
M.p.: 135°–137° C. (methanol).

The same substance was also obtained from 8-(N-benzyl-methylamino)-4-(1-oxido-thiomorpholino)-2-piperazino-pyrimido-[5,4-d]-pyrimidine (m.p.: 214°–215° C.) by refluxing with chloral hydrate in chloroform.

Example 186

2-(N-Formyl-piperazino)-4-(1-oxido-thiomorpholino)-8-phenethylamino-pyrimido-[5,4-d]-pyrimidine This compound was prepared analogous to Example 181 from 2-chloro-4-(1-oxido-thiomorpholino)-8-phenethylamino-pyrimido-[5,4-d]-pyrimidine (m.p.: 198°–200° C.) and N-formyl-piperazine.

M.p.: 204°–207° C.

Example 187

2-Piperazino-4,8-bis-(1-oxido-thiomorpholino)-pyrimido-[5,4-d]-pyrimidine

This compound was prepared analogous to Example 118 from 2-chloro-4,8-bis-(1-oxido-thiomorpholino)-pyrimido-[5,4-d]-pyrimidine (m.p.: 295°–297° C.) and piperazine.

M.p.: 251°–253° C.

Example 188

8-Benzyloxy-4-(1-oxido-thiomorpholino)-2-piperazino-pyrimido-[5,4-d]-pyrimidine

This compound was prepared analogous to Example 1 from 8-benzyloxy-2-chloro-4-(1-oxido-thiomorpholino)-pyrimido-[5,4-d]-pyrimidine (m.p.: 227°–229° C.) and piperazine.

M.p.: 212°–214° C.

Example 189

8-(4-Fluorobenzyl-thio)-4-(1-oxido-thiomorpholino)-2-piperazino-pyrimido-[5,4-d]-pyrimidine This compound was prepared analogous to Example 1 from 2-chloro-8-(4-fluorobenzyl-thio)-4-(1-oxido-thiomorpholino)-pyrimido-[5,4-d]-pyrimidine (m.p.: 192°–194° C.) and piperazine.

M.p.: 237°–239° C. (dioxane).

Example 190

8-Benzylamino-2-(N-methoxyacetyl-piperazino)-4-(1-oxido-thiomorpholino)-pyrimido-[5,4-d]-pyrimidine This compound was prepared analogous to Example 6 from 8-benzylamino-4-(1-oxido-thiomorpholino)-2-piperazino-pyrimido-[5,4-d]-pyrimidine (m.p.: 229°–232° C.) and methoxyacetyl chloride in acetone in the presence of pyridine.

M.p.: 206°–208° C. (ethanol).

Example 191

2-(N-Acetoacetyl-piperazino)-8-benzylamino-4-(1-oxido-thiomorpholino)-pyrimido-[5,4-d]-pyrimidine This compound was prepared analogous to Example 5 from 8-benzylamino-4-(1-oxido-thiomorpholino)-2-piperazino-pyrimido-[5,4-d]-pyrimidine and diketene in acetone under reflux.

M.p.: 128°–130° C.

Example 192

8-Benzylamino-2-[N-(2-furoyl)-piperazino]-4-(1-oxido-thiomorpholino)-pyrimido-[5,4-d]-pyrimidine This compound was prepared analogous to Example 190 from 8-benzylamino-4-(1-oxido-thiomorpholino)-2-piperazino-pyrimido-[5,4-d]-pyrimidine and furan-2-carboxylic acid chloride.

M.p.: 236°–238° C. (methanol/water).

Example 193

8-(N-Benzyl-methylamino)-2-[N-(2-carboxyethyl-carbonyl)-piperazino]-4-(1-oxido-thiomorpholino)-pyrimido-[5,4-d]-pyrimidine This compound was prepared analogous to Example 6 from 8-(N-benzyl-methylamino)-4-(1-oxido-thiomorpholino)-2-piperazino-pyrimido-[5,4-d]-pyrimidine (m.p.: 214°–215° C.) and succinic acid anhydride in dioxane under reflux.

M.p.: 227°–229° C. (ethanol/ethyl acetate).

Example 194

8-(N-Benzyl-methylamino)-2-(N-methoxyacetyl-piperazino)-4-(1-oxido-thiomorpholino)-pyrimido-[5,4-d]-pyrimidine This compound was prepared analogous to Example 190 from 8-(N-benzyl-methylamino)-4-(1-oxido-thiomorpholino)-2-piperazino-pyrimido-[5,4-d]-pyrimidine and methoxyacetyl chloride.

M.p.: 191°–192° C. (methanol).

Example 195

2-(N-Acetoacetyl-piperazino)-8-(N-benzyl-methylamino)-4-(1-oxido-thiomorpholino)-pyrimido-[5,4-d]-pyrimidine This compound was prepared analogous to Example 5 from 8-(N-benzyl-methylamino)-4-(1-oxido-thiomorpholino)-2-piperazino-pyrimido-[5,4-d]-pyrimidine and diketene in acetone under reflux.

M.p.: 149°–151° C. (ethanol/water).

Example 196

8-(N-Benzyl-methylamino)-2-[N-(2-furoyl)-piperazino]-4-(1-oxido-thiomorpholino)-pyrimido-[5,4-d]-pyrimidine This compound was prepared analogous to Example 190 from 8-(N-benzyl-methylamino)-4-(1-oxido-thiomorpholino)-2-piperazino-pyrimido-[5,4-d]-pyrimidine and furan-2-carboxylic acid chloride.

M.p.: 238°–240° C. (dioxane/methanol).

The compounds of the present invention, that is, those embraced by formula I above and their non-toxic, pharmacologically acceptable acid addition salts, have useful pharmacodynamic properties. More particularly, they exhibit antithrombotic activity in warm-blooded animals, such as monkeys and dogs. In addition, the compounds of this invention exhibit PDE-inhibiting activity and an inhibiting effect upon the aggregation of cancer cells entrained into the blood stream.

The antithrombotic activity and the toxicity of the novel compounds were ascertained by the test methods described below, and Tables I and II show the results of these tests for a few representative species of the genus, where A = 8-Methylthio-4-(1-oxido-thiomorpholino)-2-piperazino-pyrimido-[5,4-d]-pyrimidine, B = 8-Ethylthio-4-(1-oxido-thiomorpholino)-2-piperazino-pyrimido-[5,4-d]-pyrimidine, C = 8-Benzylthio-4-morpholino-2-piperazino-pyrimido-[5,4-d]-pyrimidine, D = 8-Benzylthio-4-(1-oxido-thiomorpholino)-2-piperazino-pyrimido-[5,4-d]-pyrimidine, E = 4-(1-Oxido-thiomorpholino)-8-(2-phenylethyl-thio)-2-piperzino-pyrimido-[5,4-d]-pyrimidine, F=8-Benzylthio-2-[N-(2-hydroxyethyl)-piperazino]-4-(1-oxido-thiomorpholino)-pyrimido-[5,4-d]-pyrimidine,
G=8-(2-Diethylaminoethyl-thio)-4-(1-oxido-thiomorpholino)-2-piperazino-pyrimido-[5,4-d]-pyrimidine,
H=8-Benzylthio-2-[N-(2-furoyl)-piperazino]-4-morpholino-pyrimido-[5,4-d]-pyrimidine,
I=8-(3,4-dimethoxybenzyl-thio)-4-morpholino-2-piperazino-pyrimido-[5,4-d]-pyrimidine,
K=8-Benzylthio-2-(N-methyl-piperazino)-4-(1-oxido-thiomorpholino)-pyrimido-[5,4-d]-pyrimidine,
L=8-(2,4-Dichlorobenzyl-thio)-4-morpholino-2-piperazino-pyrimido-[5,4-d]-pyrimidine,
M=8-Benzylthio-2-(N-formyl-piperazino)-4-(1-oxido-thiomorpholino)-pyrimido-[5,4-d]-pyrimidine,
N=8-(2-Hydroxyethoxy)-4-morpholino-2-piperazino-pyrimido-[5,4-d]-pyrimidine,
O=8-(2-Hydroxyethyl-thio)-4-(1-oxido-thiomorpholino)-2-piperazino-pyrimido-[5,4-d]-pyrimidine,
P=8-Phenylthio-2-piperazino-4-thiomorpholino-pyrimido-[5,4-d]-pyrimidine,
Q=8-Benzyloxy-4-(1-oxido-thiomorpholino)-2-piperazino-pyrimido-[5,4-d]-pyrimidine,
R=8-Benzylamino-4-(1-oxido-thiomorpholino)-2-piperazino-pyrimido-[5,4-d]-pyrimidine,
S=8-(N-Benzyl-methylamino)-4-(1-oxido-thiomorpholino)-2-piperazino-pyrimido-[5,4-d]-pyrimidine,
T=8-Benzylamino-2-piperazino-4-thiomorpholino-pyrimido-[5,4-d]-pyrimidine,
U=8-(N-Benzyl-methylamino)-2-(N-formyl-piperazino)-4-(1-oxido-thiomorpholino)-pyrimido-[5,4-d]-pyrimidine, and
V=8-Anilino-4-(1-oxido-thiomorpholino)-2-piperazino-pyrimido-[5,4-d]-pyrimidine.

1. ANTITHROMBOTIC ACTIVITY

Method

The aggregation of thrombocytes was measured according to the method of BORN and CROSS [J. Physiol. 170, 397 (1964)] in the platelet-rich plasma of healthy human test subjects. To inhibit coagulation, the blood was admixed with a 3.14% sodium citrate solution in a volumetric ratio of 1:10.

Collagen-induced aggregation

The decrease in optical density was measured and recorded photometrically after the addition of the aggregation-inducing substance. From the angle of inclination of the density curve, the rate of aggregation was estimated (Vmax). The optical density was taken as the point on the curve where the most light was transmitted (O.D.).

Small doses of collagen were chosen, but sufficient to give irreversible aggregation. (Commercial collagen of Hormonchemie, Munich, Germany.)

Before the addition of collagen, the plasma was incubated with the substance for 10 minutes at 37° C., The dosage of the test compound which produced a 50% inhibition of the thrombocyte aggregation was determined graphically ($EC_{50}$).

The following table shows the results obtained:

TABLE I

| Compound | $EC_{50}$ μmol/l |
|---|---|
| A | 0.001 |
| B | <0.01 |
| C | 0.0085 |
| D | 0.03 |

TABLE I-continued

| Compound | $EC_{50}$ μmol/l |
|---|---|
| E | 0.022 |
| F | 0.38 |
| G | 0.02 |
| H | 0.1 |
| I | 0.01 |
| K | 0.35 |
| L | 0.008 |
| M | 0.015 |
| N | 0.04 |
| O | 0.028 |
| P | ~0.1 |
| Q | 0.0036 |
| R | 0.0042 |
| S | 0.0030 |
| T | 0.25 |
| U | 0.29 |
| V | 0.03 |

2. ACUTE TOXICITY

The acute toxicity was determined in groups of 5 mice each after oral administration of a single dose of 250 mg/kg (observation time: 7 days). The test compound was suspended in 2% methyl cellulose, and after addition of some water, each substance was administered to the conscious animals by means of a stomach tube.

The following table shows the results obtained:

TABLE II

| Compound | Acute toxicity per os |
|---|---|
| C | >250 mg/kg (0 out of 5 animals died) |
| D | >250 mg/kg (0 out of 5 animals died) |
| E | >250 mg/kg (0 out of 5 animals died) |
| F | >250 mg/kg (0 out of 5 animals died) |
| G | >250 mg/kg (0 out of 5 animals died) |
| H | >250 mg/kg (0 out of 5 animals died) |
| K | >250 mg/kg (0 out of 5 animals died) |
| L | >250 mg/kg (0 out of 5 animals died) |
| M | >250 mg/kg (0 out of 5 animals died) |
| O | >250 mg/kg (0 out of 5 animals died) |
| Q | >250 mg/kg (0 out of 5 animals died) |
| R | >250 mg/kg (0 out of 5 animals died) |
| S | >250 mg/kg (0 out of 5 animals died) |
| T | >250 mg/kg (0 out of 5 animals died) |
| U | >250 mg/kg (1 out of 5 animals died) |
| V | >250 mg/kg (1 out of 5 animals died) |

Based on their pharmacological properties the compounds of general formula I as well as their physiologically compatible acid addition salts with inorganic or organic acids are suitable for the prophylaxis of thromboembolic diseases such as coronary infarct, cerebral infarct, so-called transient ischaemic attacks, amaurosis fugax as well as for the prophylaxis of arteriosclerosis and metastase formation.

For pharmaceutical purposes the compounds of the present invention are administered to warm-blooded animals perorally, perenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0014 to 0.29 mgm/kg body weight, preferably 0.007 to 0.071 mgm/kg body weight, 2 to 4 times daily.

The following examples illustrate a few pharmaceutical dosage unit compositions comprising a compound of the present invention as an active ingredient and represent the best modes contemplated of carrying out the invention. The parts are parts by weight unless otherwise specified.

Example 197

Coated tablets

The tablet core composition is compounded from the following ingredients:

| | |
|---|---|
| 8-Benzylthio-4-morpholino-2-piperazino-pyrimido-[5,4-d]-pyrimidine | 1.0 parts |
| Lactose | 30.0 " |
| Corn starch | 14.5 " |
| Polyvinylpyrrolidone | 4.0 " |
| Magnesium stearate | 0.5 " |
| Total | 50.0 parts |

Preparation:

The active ingredient, the lactose and the corn starch are intimately admixed with each other, the mixture is moistened with an aqueous solution of the polyvinylpyrrolidone, the moist mass is granulated through a 1 mm-mesh screen, and the granulate is dried. The dry granulate is admixed with the magnesium stearate, and the composition is compressed into 50 mgm-tablet cores which are subsequently coated with a thin shell consisting essentially of a mixture of sugar and talcum. Each coated tablet is an oral dosage unit composition containing 1 mgm of the active ingredient.

Example 198

Tablets

The tablet composition is compounded from the following ingredients:

| | |
|---|---|
| 8-Benzylthio-4-morpholino-2-piperazino-pyrimido-[5,4-d]-pyrimidine | 2.0 parts |
| Lactose | 29.0 " |
| Corn starch | 14.5 " |
| Polyvinylpyrrolidone | 4.0 " |
| Magnesium stearate | 0.5 " |
| Total | 50.0 parts |

Preparation:

The composition is compounded in the same manner as the tablet cores in the preceding example, and the composition is compressed into 50 mgm-tablets. Each tablet is an oral dosage unit composition containing 2 mgm of the active ingredient.

Example 199

Suppositories

The suppository composition is compounded from the following ingredients:

| | |
|---|---|
| 8-Benzylthio-4-morpholino-2-piperazino-pyrimido-[5,4-d]-pyrimidine | 5.0 parts |
| Suppository base (e.g. cocoa butter) | 1,695.0 " |
| Total | 1,700.0 parts |

Preparation:

The suppository base is melted and cooled to 38° C., the finely milled active ingredient is blended into the suppository base with a homogenizer, the composition is cooled to 35° C., and 1700 mgm-portions thereof are poured into cooled suppository molds and allowed to harden therein. Each suppository is a rectal dosage unit composition containing 5 mgm of the active ingredient.

Example 200

Suspension

The suspension is compounded from the following ingredients:

| | | |
|---|---|---|
| 8-Benzylthio-4-morpholino-2-piperazino-pyrimido-[5,4-d]-pyrimidine | 0.04 | parts |
| Carboxymethyl cellulose | 0.10 | " |
| Methyl-p-hydroxy benzoate | 0.05 | " |
| Propyl p-hydroxy-benzoate | 0.01 | " |
| Cane sugar | 10.00 | " |
| Glycerin | 5.00 | " |
| Sorbitol solution, 70% | 20.00 | " |
| Flavoring | 0.30 | " |
| Distilled water q.s.ad | 100.00 | parts by vol. |

Preparation:

The distilled water is heated to 70° C., and the p-hydroxy-benzoates, the glycerin and the carboxymethyl cellulose are dissolved therein while stirring. The solution is cooled to room temperature, and the active ingredient is homogeneously dispersed therein. The sugar, the sorbitol solution and the flavoring are added to and dissolved in the mixture, and the composition is de-aerated in vacuo while stirring. 5 ml of the suspension are an oral dosage unit composition containig 2 mgm of the active ingredient.

Example 201

Hypodermic solution

The solution is compounded from the following ingredients:

| | | |
|---|---|---|
| 8-Benzylthio-4-morpholino-2-piperazino-pyrimido-[5,4-d]-pyrimidine | 1.0 | parts |
| Acetic acid, 0.01 N | 300.0 | " by vol. |
| Sodium chloride | 18.0 | " |
| Double distilled water q.s.ad | 2000.0 | parts by vol. |

Preparation:

The active ingredient is suspended in the double-distilled water containing the sodium chloride and, while warming, the active ingredient is completely dissolved by dropwisely adding the acetic acid. The resulting solution is filtered through a membrane filter and filled into 2 cc-ampules which are subsequently sterilized in an autoclave and sealed. The contents of each ampule are an injectable dosage unit composition containing 1 mgm of the active ingredient.

Any one of the other compounds embraced by formula I or a non-toxic, pharmacologically acceptable acid addition salt thereof may be substituted for the particular active ingredient in Examples 197 through 201. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of preventing or relieving thrombosis in a warm-blooded animal in need thereof, which comprises perorally, parenterally or rectally administering to said animal an effective antithrombotic amount of a compound of the formula

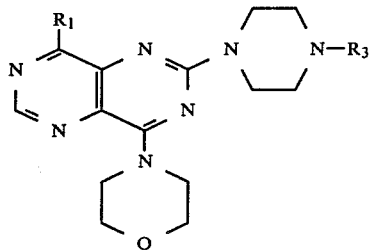

wherein $R_1$ is methoxy; ethoxy; 2-hydroxy-ethoxy; (alkyl of 1 to 8 carbon atoms)mercapto; cyclohexylmercapto; phenethylmercapto; 1-phenylethyl-mercapto; 3-phenylpropyl-mercapto; 2-diethylaminoethyl-mercapto; 1-naphthylmethyl-mercapto, furfuryl-mercapto; 2-indanyl-mercapto; (unsubstituted or mono-substituted phenyl)mercapto, where the substituent is fluorine, chlorine, bromine, methyl, hydroxyl, methoxy or amino; (unsubstituted or monosubstituted benzyl)mercapto, where the substituent is attached to the phenyl moiety and is fluorine, chlorine, methyl, hydroxyl, methoxy, nitro or trifluoromethyl; dichlorobenzyl-mercapto; methylenedioxybenzyl-mercapto; dimethoxybenzyl-mercapto; thiomorpholino; thiomorpholino-1-oxide; (unsubstituted or mono-hydroxy-substituted alkyl of 1 to 4 carbon atoms)-amino; N,N-di(unsubstituted or mono-hydroxy-substituted alkyl of 1 to 4 carbon atoms)-amino; phenyl(alkyl of 1 to 4 carbon atoms)-amino; N-(alkyl of 1 to 4 carbon atoms)-phenyl-(alkyl of 1 to 4 carbon atoms)-amino; phenyl-amino; or N-(alkyl of 1 to 4 carbon atoms)-phenylamino; and $R_3$ is hydrogen; formyl; 2-furoyl; or 2-thenoyl; or a non-toxic, pharmacologically acceptable acid addition salt thereof.

2. The method of claim 1,
where
$R_1$ is 2-hydroxy-ethoxy; (unsubstituted or mono-substituted benzyl)mercapto, where the substituent is methyl, methoxy, fluorine or chlorine; dichlorobenzylthio; dimethoxybenzylthio; benzylamino; N-methyl-benzylamino; or 2-phenylethyl-amino; and $R_3$ is hydrogen, formyl or furoyl.

3. The method of claim 1,
where
$R_1$ has the meanings defined in claim 1; and
$R_3$ is hydrogen.

4. The method of claim 1,
where
$R_1$ is benzylamino, N-methyl-benzylamino, benzylthio, dichlorobenzylthio or dimethoxybenzylthio; and
$R_3$ is hydrogen.

5. The method of claim 1, where said compound is 8-benzylthio-4-morpholino-2-piperazino-pyrimido[5,4-d]pyrimidine or a non-toxic, pharmacologically acceptable acid addition salt thereof.

* * * * *